United States Patent
Sonnenschein et al.

(10) Patent No.: US 10,188,275 B2
(45) Date of Patent: *Jan. 29, 2019

(54) SMALL DIAMETER VIDEO CAMERA HEADS AND VISUALIZATION PROBES AND MEDICAL DEVICES CONTAINING THEM

(71) Applicant: Medigus Ltd., Omer (IL)

(72) Inventors: Elazar Sonnenschein, Beer Sheva (IL); Ariel Smoliar, Rehovot (IL); Yuval Malka, Beer Sheva (IL)

(73) Assignee: MEDIGUS LTD., Omer (IL)

( * ) Notice: Subject to any disclaimer, the term of this patent is extended or adjusted under 35 U.S.C. 154(b) by 181 days.

This patent is subject to a terminal disclaimer.

(21) Appl. No.: 15/051,265

(22) Filed: Feb. 23, 2016

(65) Prior Publication Data

US 2016/0166134 A1 Jun. 16, 2016

Related U.S. Application Data

(63) Continuation of application No. 14/324,531, filed on Jul. 7, 2014, now abandoned, which is a
(Continued)

(51) Int. Cl.
*H04N 5/225* (2006.01)
*A61B 1/05* (2006.01)
(Continued)

(52) U.S. Cl.
CPC .............. *A61B 1/05* (2013.01); *A61B 1/0055* (2013.01); *A61B 1/00096* (2013.01);
(Continued)

(58) Field of Classification Search
CPC ....... A61B 1/05; A61B 1/00096; A61B 1/012; H04N 5/374; H04N 5/2257
See application file for complete search history.

(56) References Cited

U.S. PATENT DOCUMENTS

| | | | |
|---|---|---|---|
| 5,751,341 A | 5/1998 | Chaleki | |
| 6,080,101 A | 6/2000 | Tatsuno | |

(Continued)

FOREIGN PATENT DOCUMENTS

| | | |
|---|---|---|
| JP | S47-030234 | 12/1972 |
| JP | H05-305052 | 11/1993 |

(Continued)

*Primary Examiner* — Jonathan R Messmore
(74) *Attorney, Agent, or Firm* — Roach Brown McCarthy & Gruber, P.C.; Kevin D. McCarthy

(57) ABSTRACT

In a first aspect the invention is a video camera head comprising an objective lens assembly and a solid state imager (SSI) comprised of a solid state pick up device and integrated circuitry adapted to produce an output video signal. The SSI is configured to allow video signals to be sent from the SSI and power to be supplied to the SSI by means of four or less electrically connecting pads. In a second aspect the invention is a video camera head comprising a 0.7 mm×0.7 mm sensor and an integral 1.4 mm inner diameter light ring. In a third aspect the invention is a visualization probe comprising illumination means and a video camera head of the first aspect. The visualization probe has a maximum outer diameter of 2.8 mm or less. In a fourth aspect the invention is a medical device comprising a visualization probe of the third aspect. The medical device has a maximum outer diameter of 3.2 mm or less.

24 Claims, 26 Drawing Sheets

US 10,188,275 B2
Page 2

Related U.S. Application Data continuation-in-part of application No. 12/883,288, filed on Sep. 16, 2010, now Pat. No. 8,803,960.

(60) Provisional application No. 61/242,823, filed on Sep. 16, 2009.

(51) Int. Cl.
| | |
|---|---|
| *A61B 1/00* | (2006.01) |
| *A61B 1/005* | (2006.01) |
| *A61B 17/29* | (2006.01) |
| *G02B 23/24* | (2006.01) |
| *A61B 1/012* | (2006.01) |
| *H04N 5/374* | (2011.01) |
| *A61B 1/06* | (2006.01) |
| *A61B 17/22* | (2006.01) |
| *A61B 90/00* | (2016.01) |
| *A61B 90/30* | (2016.01) |

(52) U.S. Cl.
CPC .............. *A61B 1/012* (2013.01); *A61B 1/051* (2013.01); *A61B 17/29* (2013.01); *G02B 23/243* (2013.01); *H04N 5/2253* (2013.01); *H04N 5/2254* (2013.01); *H04N 5/2257* (2013.01); *H04N 5/374* (2013.01); *A61B 1/0684* (2013.01); *A61B 90/361* (2016.02); *A61B 2017/22042* (2013.01); *A61B 2090/306* (2016.02); *H04N 2005/2255* (2013.01)

(56) References Cited

U.S. PATENT DOCUMENTS

| | | | |
|---|---|---|---|
| 6,445,939 B1 | 9/2002 | Swanson | |
| 6,458,076 B1 | 10/2002 | Pruitt | |
| 6,753,905 B1 | 6/2004 | Okada | |
| 7,332,701 B2 | 2/2008 | Van Arendonk | |
| 7,409,130 B2 | 8/2008 | Hatori | |
| 7,578,786 B2* | 8/2009 | Boulais | A61B 1/00059 600/141 |
| 7,859,033 B2 | 12/2010 | Brady | |
| 7,916,300 B2 | 3/2011 | Misawa | |
| 7,923,798 B2 | 4/2011 | Minamio | |
| 7,990,453 B2 | 8/2011 | Egawa | |
| 8,368,787 B2 | 2/2013 | Iida | |
| 2003/0171648 A1* | 9/2003 | Yokoi | A61B 1/04 600/109 |
| 2005/0179805 A1* | 8/2005 | Avron | G02B 7/022 348/340 |
| 2007/0010711 A1 | 1/2007 | Hasegawa | |
| 2007/0182842 A1* | 8/2007 | Sonnenschein | A61B 1/00124 348/340 |
| 2007/0288001 A1 | 12/2007 | Patel | |
| 2008/0118241 A1 | 5/2008 | TeKolste | |
| 2008/0132761 A1 | 6/2008 | Sonnenschein | |
| 2008/0214897 A1 | 9/2008 | Matsuo | |
| 2009/0200585 A1* | 8/2009 | Nozaki | H01L 27/1464 257/292 |
| 2009/0203966 A1 | 8/2009 | Mizuyoshi | |
| 2009/0213262 A1* | 8/2009 | Singh | G02B 7/021 348/340 |
| 2009/0216220 A1 | 8/2009 | Hoey | |
| 2009/0230289 A1 | 9/2009 | LePage | |
| 2010/0249700 A1 | 9/2010 | Spivey | |
| 2011/0050874 A1* | 3/2011 | Reshef | H04N 5/374 348/65 |

FOREIGN PATENT DOCUMENTS

| | | |
|---|---|---|
| JP | 2000-019390 | 1/2000 |
| JP | 2004-337356 | 12/2004 |
| JP | 2007-236812 | 9/2007 |
| JP | 2008206624 | 9/2008 |
| JP | 2008-270650 | 11/2008 |
| WO | 2006/039646 | 4/2006 |

* cited by examiner

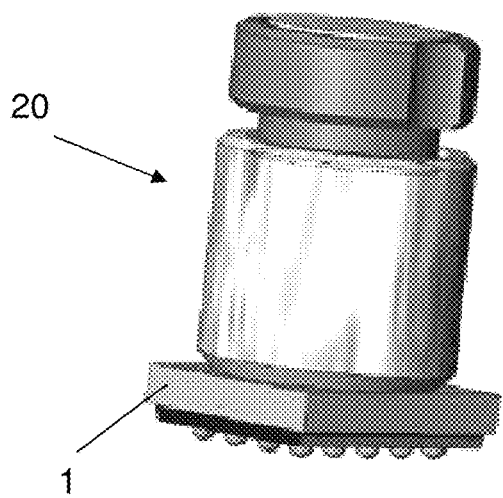
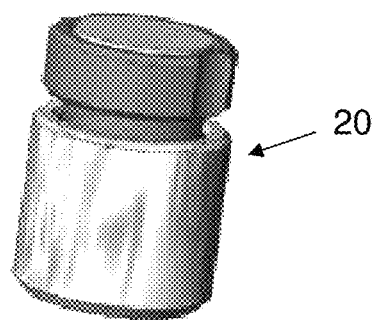
Fig. 2A    Fig. 2B
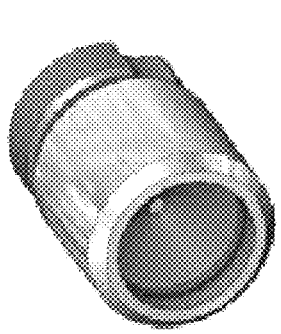
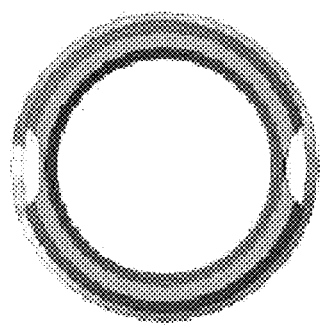
Fig. 2C    Fig. 2D
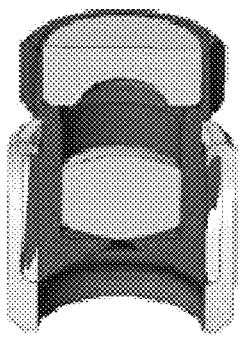
Fig. 2E

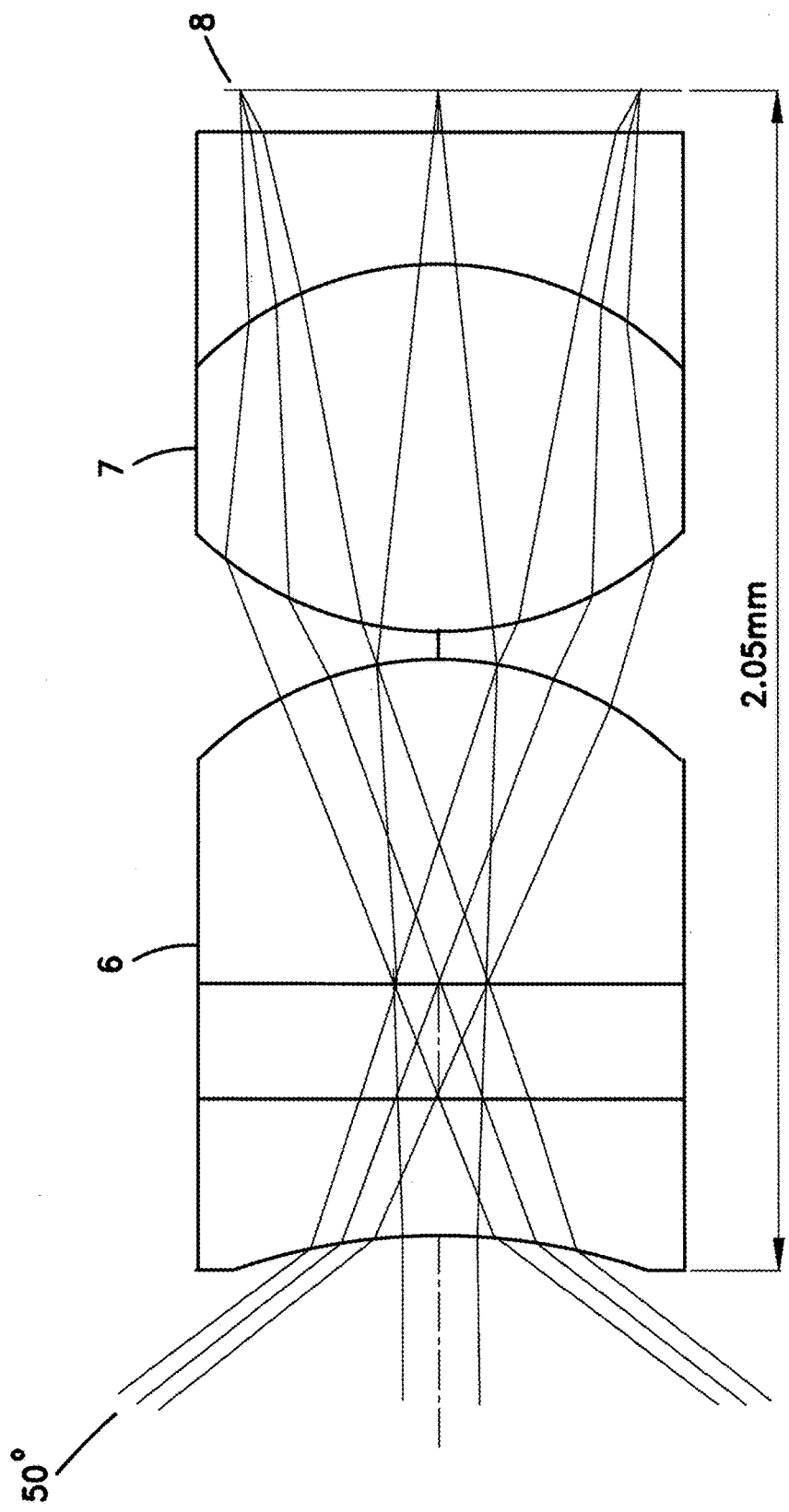

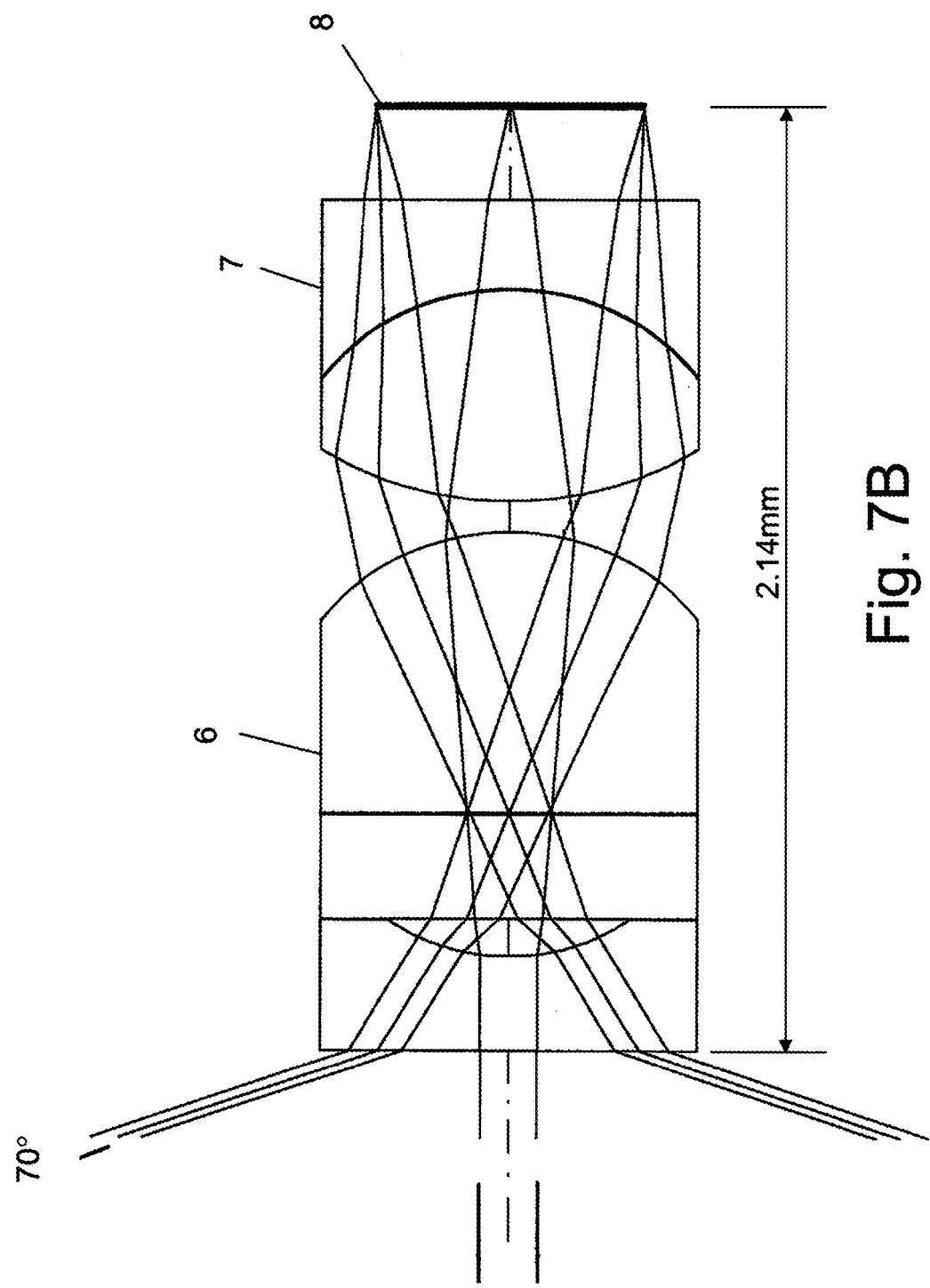

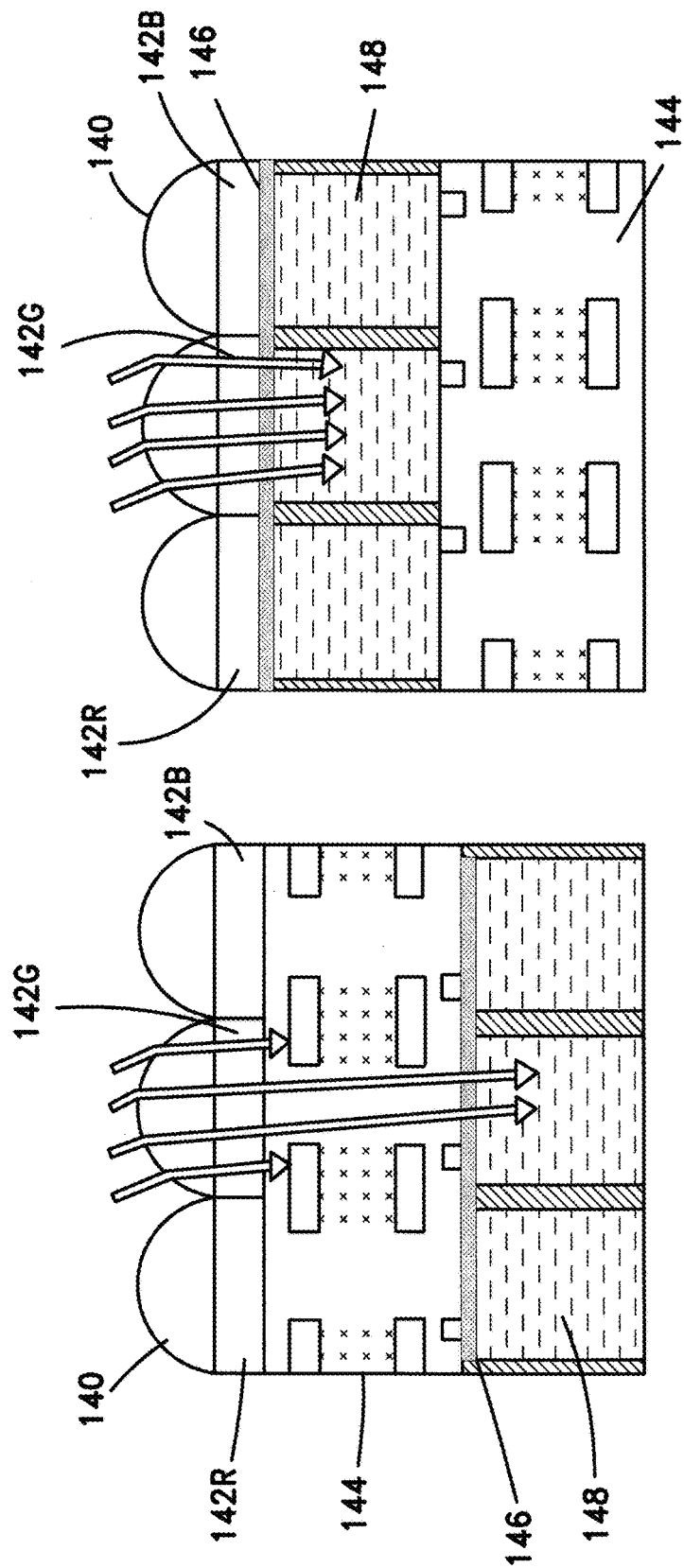

SMALL DIAMETER VIDEO CAMERA HEADS AND VISUALIZATION PROBES AND MEDICAL DEVICES CONTAINING THEM

FIELD OF THE INVENTION

The present invention relates to the field of visualization tools. More particularly, the invention relates to visualization probes useful in diagnostic, therapeutic and in surgical apparatus, as well as to a variety of non-medical (e.g., industrial) applications.

BACKGROUND OF THE INVENTION

Visualization inside the human body is an indispensable tool to enable the physician to perform an accurate diagnosis of a variety of illnesses, to deliver therapeutic agents and/or to perform minimal invasive surgical operations inside the body. Obviously to reduce trauma for the patient, such procedures are better performed through the natural orifices of the human body, whenever possible, however sometimes it is necessary to use invasive techniques and to penetrate the human body through the skin. A very large number of endoscopic devices exist nowadays. These devices, which consist of an elongated body provided with channels through which medical devices can be inserted, and fluid or air/$CO_2$/vacuum or other devices, for example for ablation, cutting, sealing, approximating tissues, etc., can be delivered or withdrawn, are introduced into the body up to the point where the procedure is to be performed. Obviously such devices can be independently used as stand-alone devices and do not necessarily have to be used through channels. Many of these endoscopic devices are provided with a built-in camera, and others have cameras introduced through channels in the body of the endoscopic device. In this context and throughout this specification, the term "endoscopic device", used in the context of medical applications, refers to any elongated device that can be inserted into human cavities, either through the natural orifices, through an incision in the skin, or first through a natural orifice and then through a incision in an internal organ. A non exclusive list will contain for example, conventional endoscopes such as colonoscopes, bronchoscopes, laparoscopes, ureteroscope, cystoscope, angioscope, durendoscope, but other devices should be also included, for example, needles, catheters, laryngoscopes, staplers, guidewires, papilotomes, cutters, balloons, forceps, trocars, etc.

As said, due to their size all the above-mentioned instruments cannot reach certain locations in the body without causing a significant trauma to the patient. Others might severely endanger the safety of the patient and due to their size might cause severe damages. Three illustrative examples are the human brain, the ear canal, and heart arteries. In an endoscopic brain surgery procedure performed through the nose, i.e., trans-nasal, it is not possible to advance one of the prior art instruments due to the dimension involved in creating a tunnel and the brain configuration. Moreover, if an instrument greater than 2 mm is introduced without a good image and superb articulation, safety and trauma issues will block it before it reaches its destination. In the second example, the Eustachian tube has a typical dimension of approximately 1.5 mm (in adults). In order to view the canal a small diameter device with good articulation is needed. The device must negotiate the turns in the anatomical configuration without causing trauma to the patient. The same problem applies to other organs as well, such as heart arteries, kidneys, common bile duct, pancreas, lungs, etc.

As said, while the invention is applicable to uses other than medical, such as veterinary, industrial, research, etc., the description to follow will be made with reference to medical applications in particular, since its relevance to other fields will be readily apparent to the skilled person. For example, industrial applications are inspection of turbine blades, of containers that contain radioactive or biologically hazardous fluids, of the interiors of very narrow pipes, or of the interior of closed containers or chambers that can only be accessed through very small diameter openings.

Cameras used in state-of-the-art endoscopic equipment are typically high-quality CCD cameras, equipped with illumination sources and optical fibers to propagate the light. These cameras require superb electronics and state-of-the-art sensors, optics and image processing, as well as hand assembly of the camera head and optics, all of which results in very expensive equipment. The resulting equipment has to be reused via sterilization because of cost considerations, which in turn entails handing costs.

In order to reduce trauma for the patients, small diameter endoscopic devices are preferred. The envelope of the device (its outer cross-section) will be defined by its internal components. Thus, in order to reduce the overall diameter of the endoscopic device, the internal components must be consequently small. This requirement dictates compromises when designing endoscopic devices, because, for example, large working channels, i.e. the pipes which enable other tools to enter the region of interest in the body through the endoscopic device without affecting the internal parts of the endoscopic device, will dictate the use of a small imager or minute cables for articulation, or minimum illumination, etc.

It is well known in the art that miniature imagers suffer from noisy images due to insufficient illumination caused by small diameter illumination fibers, VCSELs or LEDs employed. In order to overcome some of these problems, a compromise must be made based on the primary goal of the device, i.e., whether a small diameter is more important than a high-quality image, or whether minimum assembly costs must be achieved, etc. All this dictates that in order to produce a good image which is acceptable to the physician in order to be able to perform the required procedure, a quality pixel array should be employed in currently available devices. The sensor must be coupled to state of the art short length optics and provided with white light generated usually by an arc lamp such as Xenon, good illumination fiber that withstands a small diameter bending radius, and the like requirements.

The smallest available imaging sensor, the illumination means (fibers, VCSELs or LED) and the internal maneuvering means (mechanical or electrical), dictate the internal dimension of the endoscopic device. In addition, an external sheath, sometimes used in conjunction with a braid or a metal spring will dictate the external dimension, known as the Outer Diameter of the endoscopic device. Obviously in order to perform an endoscopic procedure through a natural orifice, the Outer Diameter must be small in comparison to the dimensions of the orifice itself. Thus, for example, In Ears-Nose-Throat (ENT) procedures, the dimension of an existing ENT endoscopic device will be in the range of 2-3.6 mm. Taking into account that the smallest CCD available on the market (manufactured by Sony), is in the range of 1.4 mm×1.4 mm—including its package with approximately 120K effective pixels, which of course requires a certain amount of light in order to generated an acceptable raw signal (analog) to be sent to an image processing unit which usually is located externally to the endoscopic device—it is possible to show that the minimum Outer Diameter of an endoscopic device without working channel should be in the range of the sensor's diagonal plus 0.15 mm (for wall thickness of the external sheath), i.e. 2.11 mm. Adding a working channel and another channel for irrigation/insufflations or suction will increase this diameter to a realistic diameter of 3 to 3.6 mm. On the other hand, it is possible to use the smallest available CMOS sensor for imaging purposes, hence utilizing the strength of micro electronics and cheaper production of such wafers. For example, a CMOS sensor with only 10K pixels that measures 1 mm×1 mm including CSP package (manufactured by Cypress), includes all electronics needed to generate an image (digital) to be presented on screen. Such a sensor will yield an endoscopic device with minimum Outer Diameter of 1.6 mm without any working channel but with a poor image in comparison to the CCD image. In fact, this 1 mm×1 mm with 10K pixels CMOS sensor does not provide superior performance than an imaging fiber with the same diameter however with 20K pixels. It is however smaller in diameter than the CCD sensor, and therefore may be used in a procedure where the natural orifice is small and it is possible to compromise regarding the quality of the image. As will be appreciated by the skilled person, producing miniature image sensors presents difficult design and production challenges because the yield is low, the assembly is complex and time consuming, and the sensors are expensive.

In both cases discussed above, it was assumed that the cable that connects the imager to the video processing unit or directly to the monitor is smaller than the imager itself. This however very much depends on the imager's design (analog or digital), the number of pads in the package, and its dimension. In most of the imagers available today the minimum number of pads is 6 to 24 for CMOS and 8 to 14 for CCD. Since current technologies suggest that each pad has a minimum dimension (150 to 350 microns), this affects the overall dimension of the imager, hence the endoscopic device Outer Diameter. These two extreme solutions explain the problem, on the one hand an imager that provides a good image together with some additional pipes (for working channel and/or irrigation/insufflations/suction) and illumination means requires a larger diameter endoscopic sensor and expensive components. Hence the result is an expensive endoscopic tool that must be reused in order to receive a return on investment. On the other hand is the imager that offers low resolution imaging but still results in an expensive tool due to the other components, assembling, and labor that are associated with the production of such devices.

In order to reach an optimized result, both in respect of the trauma to the patient, safe procedure, and the cost of the device—or in other words, the smallest possible Outer Dimension and the smallest incision required to introduce the device into the body, while keeping minimal cost so it can be produced as a mass production article that is disposable—a new set of problems, never before addressed in those terms in the art, must be solved.

It would therefore be desirable to provide a solution that overcomes the disadvantages of the prior art, both in respect of design, construction, functional problems and of costs of a small diameter visualization probe or endoscopic device.

It is an object of the present invention to provide such a solution, which overcomes the disadvantages of the prior art.

It is another object of the invention to provide surgical, therapeutic and/or diagnostic devices equipped with visualization means, which are relatively inexpensive.

Other objects and advantages of the invention will become apparent as the description proceeds.

SUMMARY OF THE INVENTION

In a first aspect the invention is a video camera head comprising an objective lens assembly and a solid state imager (SSI) comprised of a solid state pick up device and integrated circuitry adapted to produce an output video signal. The SSI is configured to allow video signals to be sent from the SSI and power to be supplied to the SSI by means of four or less electrically connecting pads.

In embodiments of the video camera head of the invention the objective lens assembly is implemented using wafer level technology.

In embodiments of the video camera head of the invention the output video signal is carried by an electric current.

In embodiments of the video camera head of the invention the video camera head has a maximum outer diameter of 1.4 mm or less.

In embodiments of the video camera head of the invention the electrical connections between the electrically connecting pads and the solid state pick up device are implemented by means of through silicon vias.

In embodiments of the video camera head of the invention the photosensitive elements of the solid state pick up device are implemented using back side illumination technology. These embodiments can comprise pixel cells having dimensions that are in the range of 2.2×2.2 microns to 0.9×0.9 microns.

In embodiments of the video camera head of the invention the length of the objective lens assembly is 2.5 mm or less.

Embodiments of the video camera head of the invention comprise an iris created by metalizing one surface of one lens of the objective lens assembly and etching the iris therein.

In a second aspect the invention is a video camera head comprising a 0.7 mm×0.7 mm sensor and an integral 1.4 mm inner diameter light ring.

In a third aspect the invention is a visualization probe comprising illumination means, an objective lens assembly, and a solid state imager (SSI) comprised of a solid state pick up device and integrated circuitry adapted to produce an output video signal, wherein the SSI is configured to allow video signals to be sent from the SSI and power to be supplied to the SSI by means of four or less electrically connecting pads and the visualization probe has a maximum outer diameter of 4 mm or less.

In embodiments of the visualization probe of the invention the objective lens assembly is implemented using wafer level technology.

In embodiments of the visualization probe of the invention the objective lens assembly is implemented using injected molded lenses.

In embodiments of the visualization probe of the invention the output video signal is carried by an electric current.

In embodiments of the visualization probe of the invention the electrical connections between the electrically connecting pads and the solid state pick up device and the integrated circuitry are implemented by means of through silicon vias.

In embodiments of the visualization probe of the invention the photosensitive elements of the solid state pick up device are implemented using back side illumination technology. These embodiments can comprise pixel cells having dimensions that are in the range of 2.2×2.2 microns to 0.9×0.9 microns Embodiments of the visualization probe of the invention comprise one or more of;
a) an articulation section;
b) a working channel.

In embodiments of the visualization probe of the invention the articulation section is constructed without any hinges and in one piece. In these embodiments the articulation section can be constructed from one plate and each link can be cut from the plate precisely by electromagnetic or mechanical apparatus to form a plurality of elements projecting outward from a spine and are the individual vertebrae are formed by bending the projecting elements.

In embodiments of the visualization probe of the invention the articulation section is constructed from a plurality of ring-shaped elements attached to an elongated flexible axially located component of the visualization probe/medical device, wherein the axially located component passes through the centers of the ring-shaped elements.

In a fourth aspect the invention is a medical device comprising a visualization probe comprised of illumination means, an objective lens assembly, and a solid state imager (SSI) comprised of a solid state pick up device and integrated circuitry adapted to produce an output video signal. The SSI is configured to allow video signals to be sent from the SSI and power to be supplied to the SSI by means of four or less electrically connecting pads and the medical device has a maximum outer diameter of 4 mm or less.

The medical device of the fourth aspect of the invention can be one of the following:
a. an endoscope;
b. a laparoscope;
c. a guide wire;
d. a flexible, semi-flexible, semi-rigid, or rigid single or multi-lumen tube;
e. scissors;
f. a scalpel;
g. forceps;
h. a spring;
i. a rod;
j. a device used for approximating tissues;
k. a device used for cutting tissues;
l. a device used for sealing tissues;
m. a device for burning objects;
n. a device for coagulating objects;
o. a device for feeding;
p. a device for guiding objects or substances to a location in a body;
q. a device for draining objects or substances from a location in a lumen;
r. a device for delivering objects or substances to a location in a lumen;
s. a device comprising monitoring instruments or sensors;
t. a device comprising diagnosis instruments or sensors; and
u. a wireless in vivo device.

BRIEF DESCRIPTION OF THE DRAWINGS

In the drawings:
FIG. 2A through FIG. 2E show various views of the optics which is coupled to the CMOS chip in one embodiment of the invention;
FIG. 7A illustrates an objective having a 100 degree FOV and a length of <2.05 mm from sensor surface to first lens;
FIG. 7B illustrates an objective having a 140 degree FOV and a length of <2.14 mm from sensor surface to first lens.

FIG. 27A schematically shows a pixel of a front side illumination CMOS color sensor;

FIG. 27B schematically shows a pixel of a back side illumination CMOS color sensor.

DETAILED DESCRIPTION OF THE INVENTION

Figure 1B:
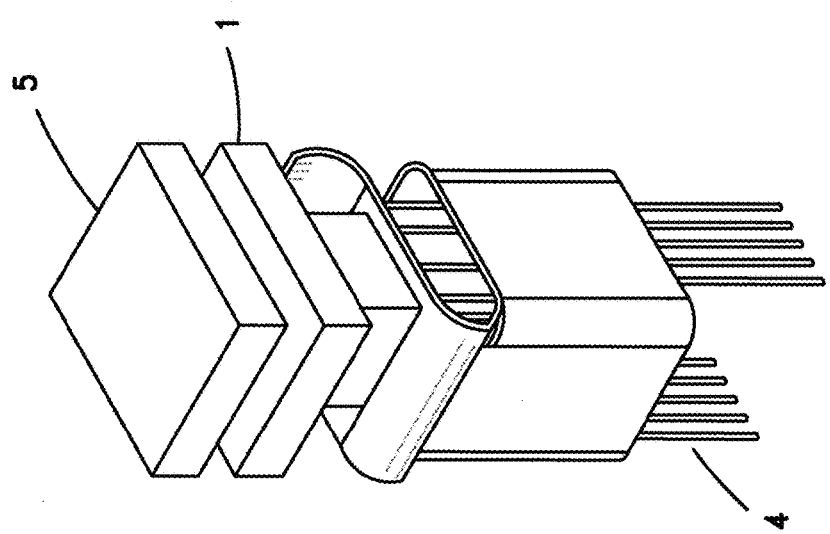
FIG. 1B shows another assembly in its completed state.

There is a considerable lack of standardization the terminology used in the literature related to digital video cameras in general and to those designed for use in endoscopic devices in particular. Herein, unless otherwise specifically mentioned, the following terminology will be used:

The terms "active area", "pixel/s area", and "array of pixels" are used interchangeably to refer to the light receiving surface of the array of photosensitive elements, e.g. photodiodes, that convert the incoming light into electrons.

The terms "sensor", "chip", "solid state image pick up device", and "image pickup device" are used interchangeably to refer to the active area; to the array of microlenses that concentrate the incoming light onto the photodiodes; to the array of filters, in the case of a color sensor; and to the silicon substrate on which the active area is created. In the case of sensors manufactures by a CMOS process, these terms also can include electronics adapted to deal with the output signals of the photodiodes that are implemented together with the array on the silicon.

The term "solid state imager" or in brief, "SSI", as used herein, indicates any suitable solid state image pick up device (for instance a CMOS or a CCD) that includes additional electronic circuits to generate additional functions of processing the signal on the same silicon or as an additional layer, where all layers are connected and integrated into the SSI.

The term "camera head" refers to the SSI and associated optics required to focus the light on the active area encapsulated in a single package.

The terms "video camera" and "camera are used interchangeably to refer to the camera head alone and also to the camera head and an additional electronic driver, if one is present.

The term "camera" refers exclusively to video cameras.

In the context of the present application the term "effective diameter" refers to the final diameter of the probe, regardless of its shape. Although in most cases the final shape of the probe would be circular, in spite of the fact that the SSI typically has a square or rectangular configuration, any other shape is possible and therefore the effective diameter could be equal to the longest cross-sectional dimension of the probe. Thus, for instance, for a probe having a square cross-section the effective diameter will be equal to the diagonal of the square, and the same arguments apply, mutatis mutandis, for a rectangular shape, an oval shape (see for example FIG. 21) or a non completed oval shape.

According to an embodiment of the invention the probe comprises electronic circuitry (or driver), which is required to elaborate the signal generated by the SSI. In most of the cases the advantage of using a CMOS as an SSI, over the CCD, is the fact that it is easier and less expensive to implement several electronic circuits that embody several important features that are needed to generate the image or other features of digital processing—for example, correlated double sampling (CDS), A/D, gain, etc. These circuits are added in the design with the pure sensor that is built from pixels that are implemented with transistors in one package. The implementation of these pixels could be based on 2 transistors per pixel, 3, 4, 5, 6 and more or by using shared transistors or other designs, for example 2T2S or 4T4S, or higher degree shared transistors that implement the pixels. Obviously, these circuits extend the dimensions of the package and add more pads. In addition, if using signals with higher clock rate, it is advisable to use a driver that contains an amplifier or a regulator, a few capacitors for noise reduction, and some resistors to match signals. Such electronic circuitry (drivers) will add space in the package or the silicon and therefore in some of the cases it will be implemented externally to the packed CMOS or CCD or as an additional layer in the silicon construction.

If the SSI has a diagonal smaller than 1.0 mm, the driver may contain parts or all of the image processing features, for example, correlation double sample (CDS) unit or other features needed to generate the image that were implemented in the packaged CMOS sensor itself and now are shifted externally to the driver or to the image processing unit. In addition, the SSI will includes all means to pump out the signal in a differential way to eliminate electronic noises. In other embodiments the CMOS sensor will contain only the implementation of minimal circuits that are needed to provide the signals and to pump out the raw signal from the CMOS. In addition, the driver will contain the minimum components required to match the clock signal needed to activate the CMOS and to pump the signal out to a video processing unit that now contains all needed circuits and components for processing the raw signal and transforming it to a video signal.

In this way, the CMOS sensor acts almost as a pure imager that transforms photons into electrons and its size is minimal. Since the driver also comprises the minimal number of components (one or two and sometimes the number could be zero), this insures that the overall dimension of the new packaged CMOS video camera is minimal. The additional problem to overcome is the number of pads associated with the CMOS design and the cable (that contains all wires) which serves to provide the signals to activate the CMOS and to pump the signal out to the video processing unit. In the common practice there are several wires to provide these services For example, in a CCD produced by SONY (e.g., ICX256 or ICX 257 or ICX 421) there are 10 pads, as seen in Table 1 below.

TABLE 1

| Pin No. | Symbol | Description |
| --- | --- | --- |
| 1 | $V_{\phi 2}$ | Vertical register transfer clock |
| 2 | $V_{\phi 1}$ | Vertical register transfer clock |
| 3 | GND | GND |
| 4 | $V_{DO}$ | Supply voltage |
| 5 | $\phi SUB$ | Substrate clock |
| 6 | $V_{OUT}$ | Signal output |
| 7 | $\phi RG$ | Reset gate clock |
| 8 | $H_{\phi}$ | Horizontal register transfer clock |

TABLE 1-continued

| Pin No. | Symbol | Description |
|---|---|---|
| 9 | $V_{\phi 3}$ | Vertical register transfer clock |
| 10 | $V_{\phi 4}$ | Vertical register transfer clock |

For the ICM105A CMOS produced by IC-Media, there are 48 pads (Table 2):

TABLE 2

| Pin # | Name | Class* | Function |
|---|---|---|---|
| 14 | CLKSEL | D, I, N | Clock source selection. 0: internal oscillator, 1: CLKIN |
| 11 | CLKIN | D, I, N | External x2 clock source |
| 12 | XIN | A, I | Oscillator in |
| 13 | XOUT | A, O | Oscillator out |
| 34 | PCLK | D, O | Pixel clock output |
| 36 | OEN | D, I, N | Output enable. 0: enable, 1: disable |
| 32 | I2CID | D, I, N | Lsb of I2C slave address |
| 33 | I2CMS | D, I, U | I2C master/slave selection. 0: slave, 1: master (auto load from EEPROM after reset) |
| 2 | SCL | D, I/O | I2C clock |
| 1 | SDA | D, I/O | I2C data |
| 10 | POWERDN | D, I, U | Power down control, 0: power down, 1: active |
| 16 | RSET | A, I | Resistor to ground = 39 KΩ @ 27 MHz main clock |
| 8 | RSTN | D, I, U | Chip reset, active low |
| 48 | DOUT[7] | D, O | Data output bit 7 |
| 47 | DOUT[6] | D, I/O | Data output bit 6; if pulled up/down, the initial value of TIMING_CONTROL_LOW[2] (VSYNC polarity) is 1/0 |
| 46 | DOUT[5] | D, I/O | Data output bit 5; if pulled up/down, the initial value of TIMING_CONTROL_LOW[1] (HSYNC polarity) is 1/0 |
| 44 | DOUT[4] | D, I/O | Data output bit 4; pulled up/down, the initial value of AD_IDL[3] (Sub ID) is 1/0 |
| 41 | DOUT[3] | D, I/O | Data output bit 3; pulled up/down, the initial value of AD_IDL[2] (Sub ID) is 1/0 |
| 39 | DOUT[2] | D, I/O | Data output bit 2; pulled up/down, the initial value of AD_IDL[1] (Sub ID) is 1/0 |
| 38 | DOUT[1] | D, I/O | Data output bit 1; pulled up/down, the initial value of AD_IDL[0] (Sub ID) is 1/0 |
| 37 | DOUT[0] | D, I/O | Data output bit 0; if pulled up/down the synchronization mode is in master/slave mode which requires HSYNC and VSYNC operating in output/input mode |
| 3 | HSYNC | D, I/O | Horizontal sync signal |
| 5 | VSYNC | D, I/O | Vertical sync signal |
| 35 | FLASH | D, O | Flash light control |
| 15 | RAMP | A, O | Analog ramp output |
| 7, 31 | VDDA | P | Sensor analog power |
| 9, 30 | GNDA | P | Sensor analog ground |
| 2 19 | VDDD | P | Sensor digital power |

In another example, for the Agilent ADCM 1650-3011, there are 18 pads (Table 3):

TABLE 3

| Location | Signal Name | Type | Description | Notes |
|---|---|---|---|---|
| 1 | GND | Common | System Ground | |
| 2 | MCLK | Input | Module Clock | |
| 3 | VSYNC | Output | Vertical Synchronization | [End_of_Frame] |
| 4 | DATA0 | Output | Parallel Data 0 | |
| 5 | DATA1 | Output | Parallel Data 1 | |
| 6 | DATA2 | Output | Parallel Data 2 | |
| 7 | DATA3 | Output | Parallel Data 3 | |
| 8 | DATA4 | Output | Parallel Data 4 | |
| 9 | DATA5 | Output | Parallel Data 5 | |
| 10 | DATA6 | Output | Parallel Data 6 | |
| 11 | DATA7 | Output | Parallel Data 7 | |
| 12 | VCLK | Output | Video Clock | [Data_Ready] |
| 13 | HSYNC | Output | Horizontal Synchronization | [End_of_Line] |
| 14 | ON/OFF | Input | Voltage Regulator Control | |
| 15 | SCLK | Input | Serial Interface Control Clock | |
| 16 | SDATA | Input/Output | Serial Interface Control Data | |
| 17 | $V_{CC}$ | Input | Voltage Input | |
| 18 | GND | Common | System Ground | |

Since in a solid state imager with a diagonal smaller than 1.0 mm there is not sufficient space for so many pads, in order to overcome this problem it is necessary to set a minimal number of pads (ideally, one pad). By multiplexing several signals using the same pad it is possible to use only 4 pads and sometimes 3 pads for the entire SSI. If the signal is pumped out in a differential way, two pads will serve for this features but it is also possible to multiplex the differential signal on one pad. Subtraction of signals will reduce noise and increase signal to noise ration.

Another way of reducing the imager's area to a minimum is to change the methodology of the output video signal of the imager by using a current method instead of a voltage method. This also dictates that the external driver should include a matching stage circuit. The benefits from using such a method include better filtering of the noise associated with amplification and the ability to transmit the video signals over longer distances by using regulators controlled by the video processor to compensate for the video signal drop.

Figure 25:
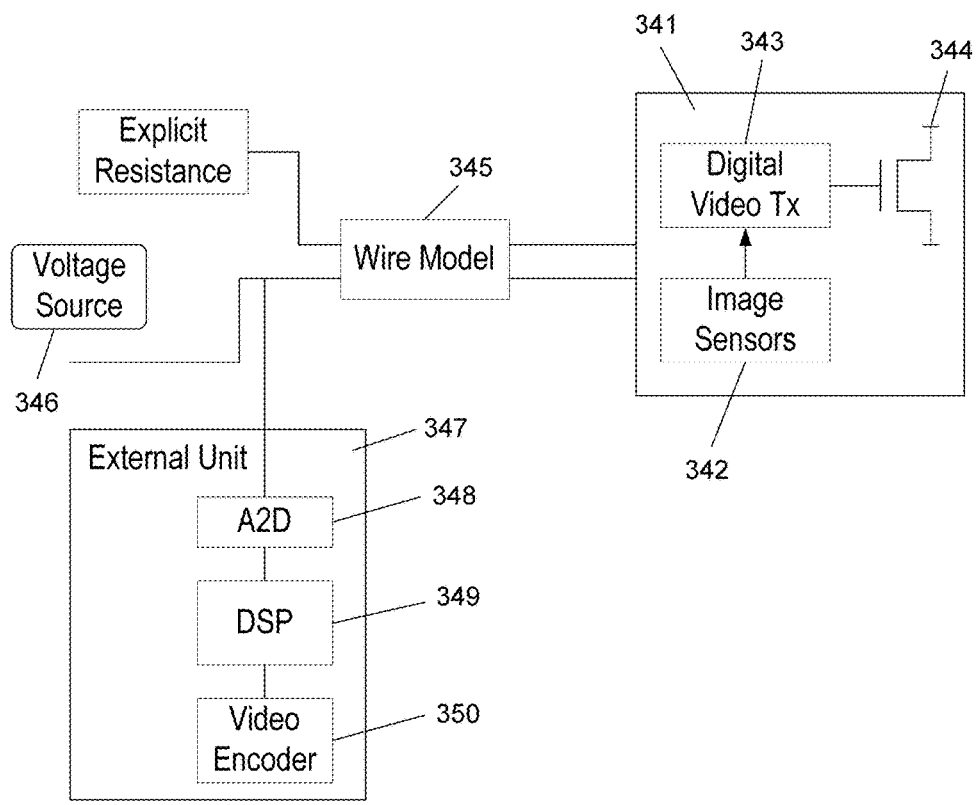
FIG. 25 is a simple diagram illustrating a silicon chip having two functions.

Another example of a way in which the dimensions of a SSI can be reduced is to provide components on the silicon that have two functions, i.e. to grab the image and to transmit it. FIG. 25 is a simple diagram that illustrates this embodiment of the invention. In the figure is seen silicon chip 341 on which is created image sensor (or SSI) 342, video transmitter 343, and transistor 344. Voltage source 346 supplies power to chip 341 through wire model 345 and is also connected to external unit 347 that comprises an analog to digital converter 348, digital signal processor 349, and video encoder 350. The chip works as follows:

1. Phase 1: Image sensor 342 grabs the image and latches it.
 2. Phase 2: Video Tx 343 transmits the image while the rest of the chip is quiet and does not generate noise.

Wire Model 345 is a wire that can be implemented by regular wires or, in this example, by using printed circuit technology and/or using laser trimming for accurate capacitance and resistance. Since there is no actual wire for the video out, the video transmitter 343 is connected to a transistor 344 which just draws current. By sending a video image, which is a stream of bits, from Video Tx 343 to transistor 344 a current signal is generated, which translates to noise on the voltage supply 346 (especially if it has explicit resistance). By measuring the Voltage of the power supply, the video bit stream inside the chip can be determined. The bit stream can be generated as slowly as desired to fit the channel behavior of the noise. It is thus possible according to the invention to send out information from the chip in a simple and efficient manner and by use of a minimal number of pads.

FIG. 28 shows actual front (top) view and back (bottom) view images of one possible implementation of a 0.7 mm×0.7 mm CMOS sensor with four pads and TSV connections. This sensor is used in visualization probes according to the invention. As will be apparent to a skilled person, the electrical connections between the circuitry created on the front side of the sensor to the external electrical components that supply power to the sensor and receive video signals from it are made using the through silicon via (TSV) technique, in which small diameter holes are created through the silicon and then filled with a conducting material. The use of TSV allows vertical routing of the conductors without increasing the overall dimensions of the sensor. As is seen in the bottom image of FIG. 28, the back side of the silicon substrate of the sensor is patterned to provide electrical conductivity between the bottoms of the vias and either conducting balls or pads, depending on if a ball grid array (BGA) or line grid array (LGA) connection arrangement will be used. Although FIG. 28 shows four pads, it is easy to show that the number of pads can be reduced to three using multiplexing.

Figure 28B:
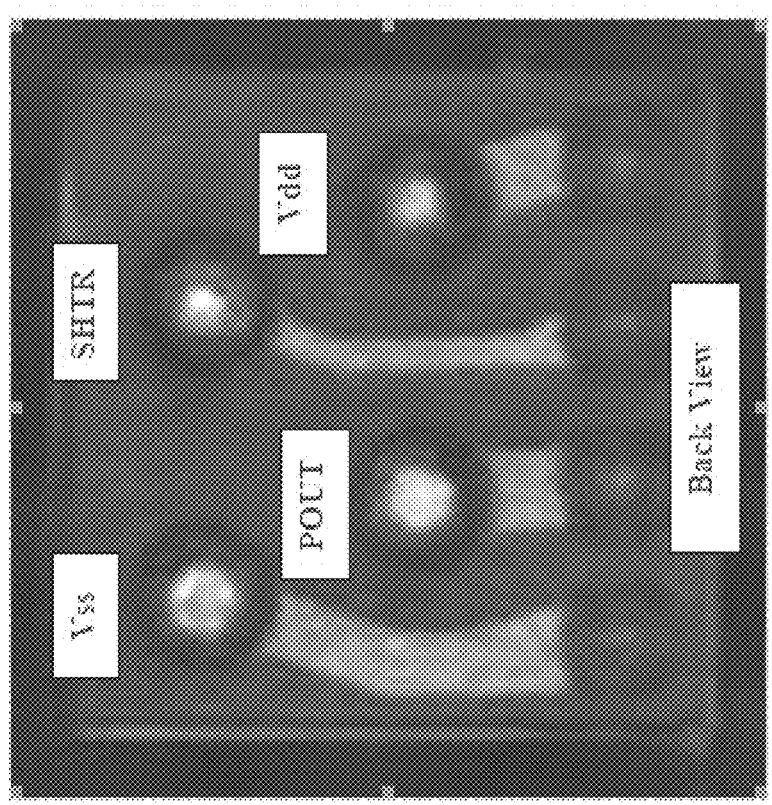
FIG. 28A and FIG. 28B show respectively actual front view and back view images of a 0.7 mm×0.7 mm CMOS sensor used in visualization probes of according to the invention.
Figure 28A:
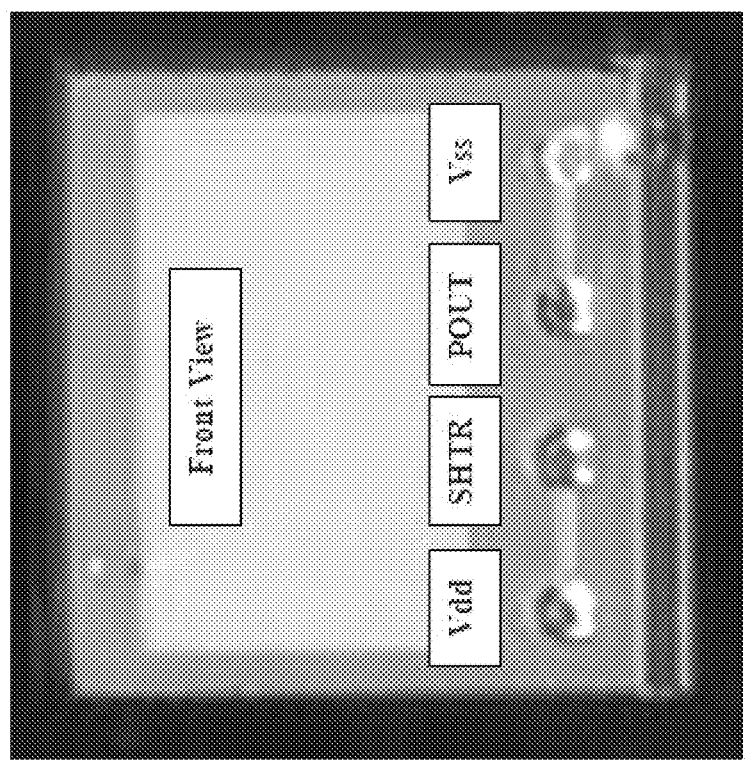

The sensor shown in FIG. 28A and FIG. 28B could employ the current methodology described herein above. For this purpose the four pads will respectively be defined as: Voltage in Vdd, Ground Vss, shutter timing SHTR, and video signal output current POUT. SHTR allows the shutter time, i.e. the time of collection of electrical charge in the pixels, to be adjusted; however in many circumstances this parameter need not be changed and a predetermined value can be determined and implemented in the circuitry on the silicon. In this case the number of pads can be reduced to the minimum value of three. In fact by using the current method for outputting the video signal and multiplexing it is theoretically possible to reduce the number of pads to two.

In view of these solutions, i.e. current video signals and TSV, the Outer Diameter of any endoscopic device built with this camera will be minimal. It is to be noted that the reason for reducing the diameter of an endoscopic device to enable the device to pass through small diameter openings or channels. Generally a circular shape is considered, however in some cases the opening has a generally elliptical shape. In these cases, a rectangular sensor can be used and the distal end of the visualization probe can by have an oval shape to better match the opening and still have enough space inside to contain all of the necessary components.

Figure 11:
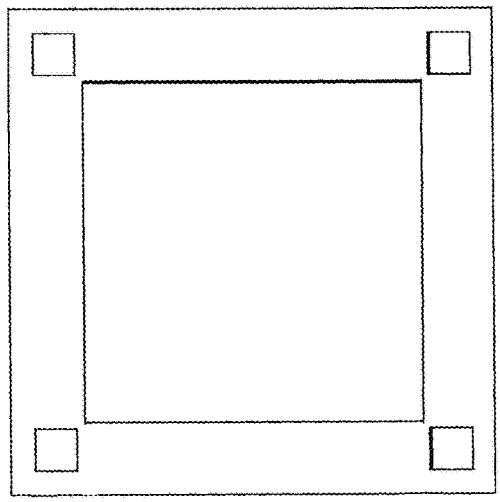
FIG. 11 shows a Solid state imager with maximum dimensions 700 microns×700 microns including package with 4 pads for electrical signals.

FIG. 11 schematically shows the layout of a solid state imager with dimensions 700 microns×700 microns including a package with 4 pads and TSV for electrical signals. In this case the active area is smaller than 500 microns×500 microns. The SSI can be produced with different sized pixel cells. For example: for 2.2 micron×2.2 micron cells it will contain 50176 pixels (224×224); for 1.75 micron×1.75 micron cells it will contain 81225 pixels (285×285); for 1.4 micron×1.4 micron cells it will contain 127449 pixels (357×357); and for 0.9 micron×0.9 micron cells it will contain 308025 pixels (555×555).

Figure 12:
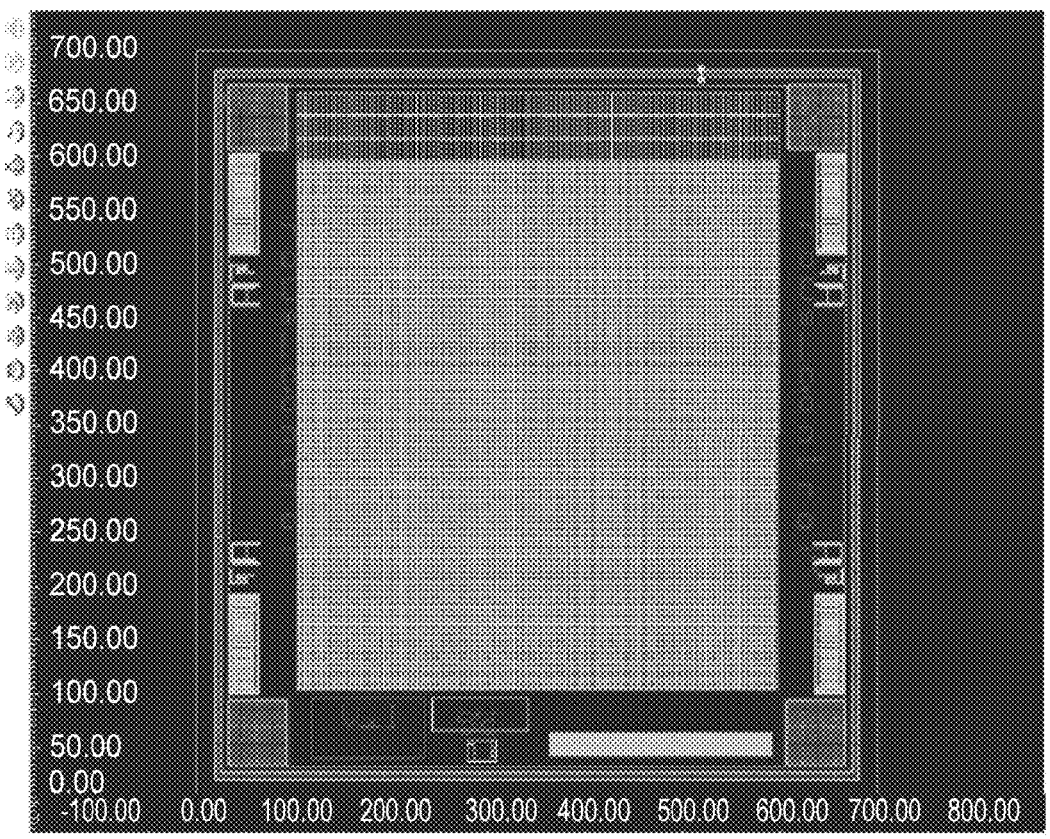
FIG. 12 shows the pixels of the Solid state imager of FIG. 11.

FIG. 12 shows the pixels of the solid state imager of FIG. 11. The imager can comprise a glass to cover the pixels and micro lenses but can also be designed to not include a glass cover and instead to comprise a 0.5 to 1.2 micron top coat (polymer) layer.

All video cameras for medical devices known to the inventor make use of what is known in the art as front side illumination (FSI) technology to produce the CMOS image pickup device. FIG. 27A schematically shows a pixel of a FSI CMOS color sensor. The colors are achieved by use of what is known in the art as Bayer filter. In a FSI sensor the photodiodes 148 comprising active areas 146 are created in the silicon substrate. On top of the active area is constructed the electrical circuit layer 148 that comprises electronic components and metal wiring. Red, green, and blue color filters 142R, 142G, and 142B are placed over the electrical circuit layer and microlenses 140 are placed on top of the filters. This type of structure suffers from many drawbacks the most obvious of which, as can be easily understood by looking at FIG. 27A, is that at least a part of the incoming light encounters elements of the electrical circuit in layer 144 and either never reaches the active area 146 or is deflected onto the neighboring photodiode. In the former case this may mean that not enough light falls on the photodiodes and in the latter case a blurry image will be recorded. The easiest solutions to these problems is to increase the amount of illumination and/or to increase the cross-sectional area of the pixels to allow more room for "free passage" of the light from the microlens to the photodiode. Neither of these solutions is compatible with the goals of the present invention since the former requires increasing the diameter of the probe in order to accommodate more or larger diameter optical fibers or LEDs and the latter either means that either the diameter of the sensor must be increased or the total number of pixels reduced, which will affect the resolution of the images.

In order to overcome these and other difficulties associated with the FSI structure it is proposed in this invention to make use of a relatively new principle of producing a pixel known as back side illumination (BSI). A BSI pixel is constructed dramatically differently from a FSI pixel and this difference enables 100% light collection by the photodiodes. FIG. 27B schematically shows the BSI structure. In BSI pixels the order of the electrical circuit layer 144 and photodiode 148 layers is reversed and all of the light entering microlens 140 is refracted directly onto the active area 146 of the corresponding photodiode after passing through the color filter.

A BSI pixel requires significantly less light, thus it is much more sensitive than a FSI pixel. Additionally BSI enables much more accurate color in comparison to the FSI pixel because there is no scattering by the components of the metallization layer. More importantly BSI enables production on the same area of many more pixels than FSI for the same amount of light or to further decrease the imager area without affecting its performance in comparison to imagers that employee FSI pixels. For medical devices, BSI provides a large advantage since it enables reduction of the diameter of the medical devices without compromising the image quality. Thus, the CMOS sensor and/or the SSI are designed and constructed differently. Adding suitable optics, which are optimal for the new conditions, yields an optimal video camera in terms of dimensions and image quality.

In one embodiment of the invention the probe is pluggable into a medical device. According to this embodiment, therefore, it is possible to provide medical devices which are reusable, i.e., which can be sterilized and used in subsequent procedures, while the visualization probe can be disposable. This is made possible by the low cost attainable by employing the methods described herein to manufacture embodiments of visualization probes according to the invention.

In another aspect, the invention is directed to a medical device comprising a socket or channel suitable to house a visualization probe having an imager with a maximum outer diameter of 1.1 mm. In such a device the socket may comprise signal transfer connectors adapted to receive signals generated by the probe and to transmit them to display equipment.

The term "medical device", as used herein, refers not only to devices which are used to actively perform surgical procedures on the human or animal body, but also to devices which are used for diagnostic purposes only and to devices used for delivery of therapy and/or food and/or drugs. Any device which is introduced into a natural or generated cavity of an animal or human body comes under the definition of medical device throughout this specification. Such medical devices may be selected, for instance, from among endoscopes; scissors; scalpels; laparoscopes; flexible, semi-flexible, semi-rigid, or rigid single or multi-lumen tubes (or pipes), used for therapeutic procedures or to protect the human body when inserting and extracting other devices through these tubes (or pipes); springs; rods; devices that are used for approximating, cutting, and sealing tissues; devices for burning, coagulating, or in other ways destroying objects; devices for feeding, guiding, draining, or delivering objects or substances; guidewires, forceps, monitoring and/or diagnosis devices; wireless in vivo devices, etc.

The invention further encompasses the combination of a medical device and of a probe as described above. For example the solid state imager can be located at the distal end of a visualization probe that is attached to a surface of the medical device.

Figure 3A:
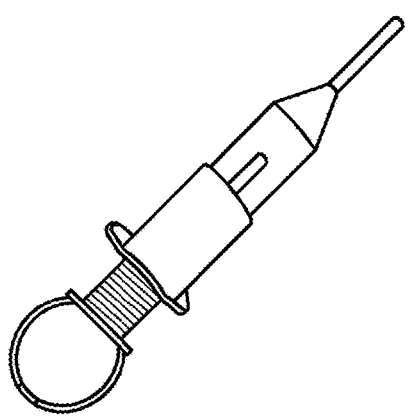
FIGS. 3A through 3E illustrates a small-diameter medical device.
Figure 3B:
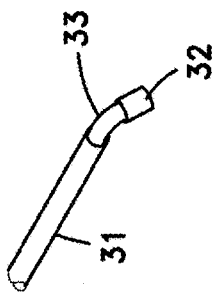

Turning now to FIG. 3A, a schematic illustration is given of an endoscopic device of a generic type, which can be used for a variety of medical applications. The device is constructed of a handle portion (FIG. 3B), to which is attached an elongated portion 31, provided with a tip 32 (FIG. 3C), shown in an enlarged view in FIG. 3D. Tip 32 can be fixed or can be connected to a bendable member 33, as in FIG. 3E.

Figure 3C:
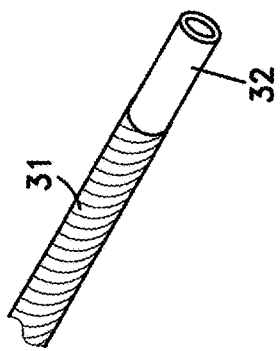
Figure 3D:
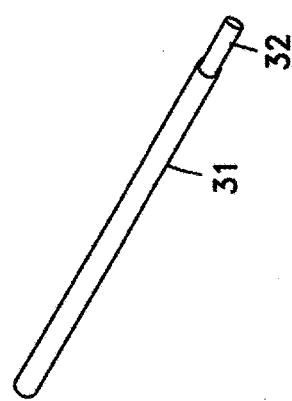
Figure 3E:
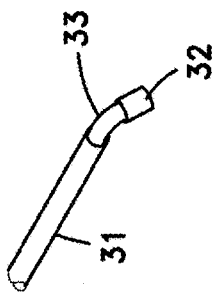
Figure 4A:
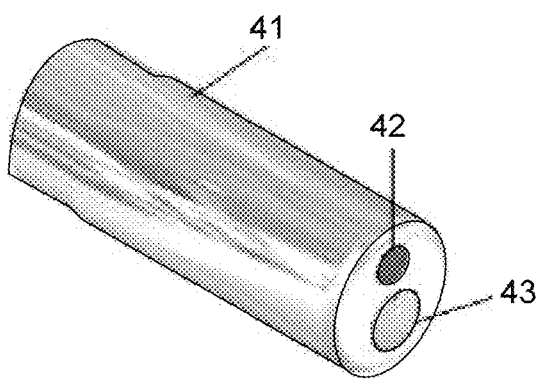
FIGS. 4A through 4C illustrates various configurations of tips of surgical or therapeutics devices embodying a probe according to the invention.
Figure 4B:
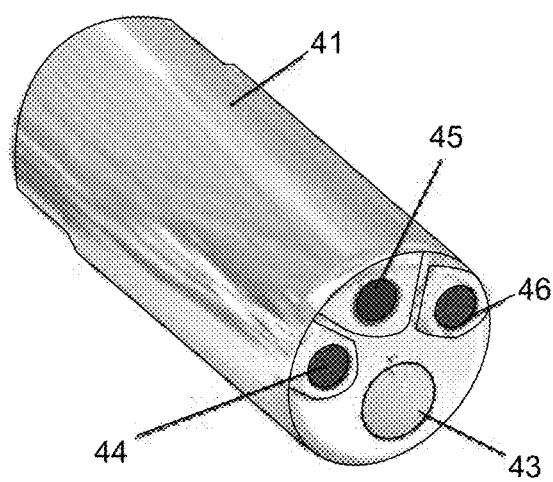
Figure 4C:
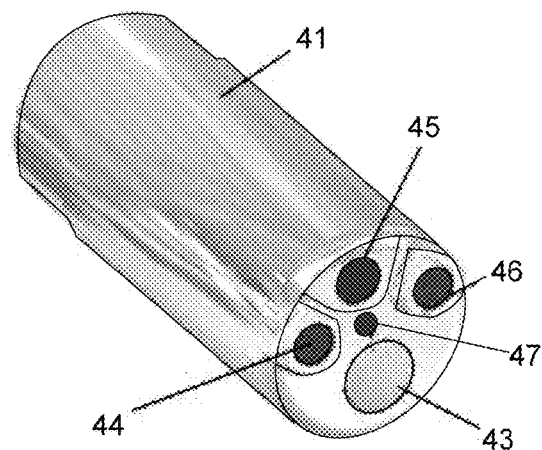

FIGS. 4A to 4C illustrate three different options for tip 32 of FIGS. 3C to 3E. FIG. 4A shows a tip 41, provided with a working channel 42 through which tools can be introduced or liquids or gases can be supplied or withdrawn. A visualization probe 43 is housed in a socket (not shown). Similarly, in FIG. 4B the tip is larger and, in addition to visualization probe 43 it also comprises three working channels 44, 45 and 46. Likewise, in FIG. 4C four different working channels are provided, 44, 45, 46 and 47.

In the embodiments shown in FIGS. 4A through 4C the source of illumination for the camera is not shown however it can be implemented as illumination fibers, one or more LEDS, lasers, VCSELs, or an array of MicroLEDs implemented through working channels or implemented on the distal face as an integral part of the device. In FIG. 4A, for example, there is one working channel and the other one is used for camera and light, which is implemented by a ring of optical fibers surrounding the objective lens in socket 43. For example, the camera head inserted into socket 43 can comprise a 0.7 mm sensor and an integral 1.4 mm inner diameter light ring.

Herein the term MicroLED is used to distinguish LEDs having a diameter in the range of 5 to 50 microns from larger LEDs. MicroLeds are usually arranged in an array to produce sufficient light while being able to fit into small "empty" spaces around the camera, thereby allowing the overall diameter of the visualization probe or other medical device to which the camera of the invention is attached to be minimized.

Figure 5A:
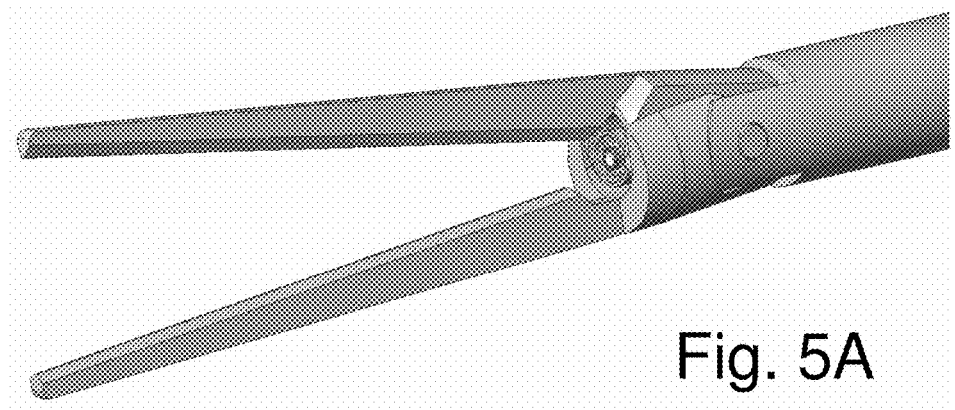
FIG. 5A to FIG. 5C schematically show surgical scissors and surgical forceps embodying a probe according to the invention.
Figure 5B:
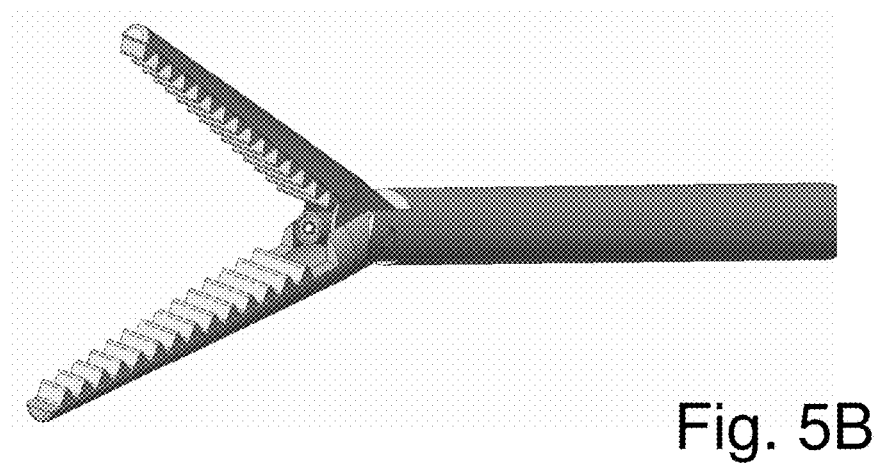
Figure 5C:
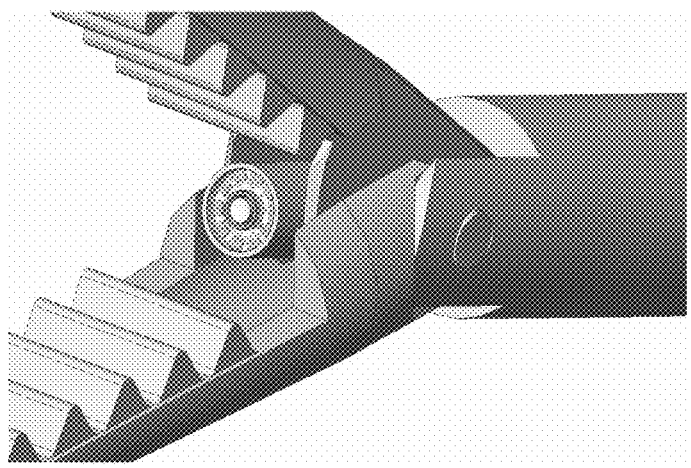

FIG. 5A schematically illustrates a surgical scissors, provided with a socket between the two blades of the scissors in which is housed a visualization probe such as described above. Accordingly, when the surgeon operates the scissors he is able to see exactly what the tip of the tool sees, as the image is transmitted to image processing and display apparatus via a data line which passes through the body of the device, to reach the socket. FIG. 5B schematically illustrates a surgical forceps provided with a visualization probe. FIG. 5C is an enlarged view of the area between the jaws of the forceps of FIG. 5B showing an array of MicroLEDs arranged to form a ring surrounding the objective lens of the camera head.

In order to enable efficient maneuvering through an incision or natural orifice with minimal trauma to the patient, particularly when the orifice is narrow, say less than 3 mm, every tool requires some type of articulation section to negotiate the entrance and the different paths. The requirements from such a section are to be flexible enough to articulate on one hand and stiff enough for rotation (without breaking) on the other hand. A smooth transition of the articulation section from a straight position to full angulations without any step (jump) is mandatory; otherwise, during maneuvering it might severely harm the tissue. In addition, due to internal turns in the body cavities or the internal organs into which the tool is advanced, short articulations must be considered. As an example, in most of the flexible endoscopes for upper or lower GI procedures, bronchoscopy or urology, each flexible endoscope will contain an articulation section (having a length from 20 mm and up to 120 mm) to enable such maneuvering. Therefore the vertebrae (articulation) section is constructed to include several links having wall thickness of 0.3 mm to 1.5 mm that provide the flexibility or rigidity as necessary. The bending radius is usually 10 mm to 60 mm and strong hinges typically having diameters of 0.8 mm to 2 mm connect the links to one another and provide the stiffening during rotation of the tool and the vertebrae. The number of links determines the bending radius; the overall diameter of the bending section and the wall thickness provide the flexibility/rigidity and force resistance. As these links are produced separately, the final angle between each link, the wall thickness and the hinge connecting two links determine the final bending radius and the forces to be applied in order to achieve the maximum angulations (up/down). It is evident that in order to construct a smooth arc from the links, it must contain a fair number of links which will require many items, a fair amount of assembly time, and might weaken the entire bending section.

For a small natural orifice or incisions in the range 1 to 3 mm, such a vertebrae concept cannot be used. It is necessary to provide an articulation section that has a short length with a bending radius smaller than 15 mm, and in some cases smaller than 3 mm, with a link that is constructed with a thin wall thickness and without any hinges since the hinges block the cross section because of their size or their weakness in the case of a very small diameter. In addition, due to its small size, it is not possible to use thicker cables; hence the forces to be applied for maximum angulations are fairly low.

Another set of problems is related to the assembling of such vertebrae, should the prior art concept be used as in standard large diameter endoscopes, it is a straightforward process to assemble large links (diameter 3.2 mm to 10 mm) with hinges (diameters of 0.8 mm to 2 mm), however when the link becomes small (diameter 1 mm to 3 mm) it is a difficult task if not impossible, and is certainly not accurate and requires several tools, as well as close inspection to produce the same articulation section each time.

In order to overcome these problems, articulation sections have been invented which are constructed without any hinges and in one piece, bent to the desired shape (circle, oval or any other undefined shape). An illustrative example of an articulation section, which allows two-way bending, is described with reference to FIGS. 16 through 18B.

In this embodiment the entire articulation section is constructed from one plate 226, with thickness of, for example, 0.04 mm. Each link is cut precisely by electromagnetic or mechanical apparatus to form a plurality of elements 228 arranged in two rows and projecting outward from spine 230. An illustrative and non-limitative list of suitable methods include laser, punch, plasma, ultrasound, wire, etc. The dimensions of the link define:
 a. The bending radius of the entire section
 b. The flexibility
 c. The maximum articulation angles (full angulations—up/down).
 d. The stiffness (by the backbone along all links)

The projecting elements 228 are then bent to form the individual inks (vertebrae) 234 that make up the articulation section. The section can be bent into a desired shape to construct the one piece articulation in one step, or more if the shape is more complex.

Figure 17:
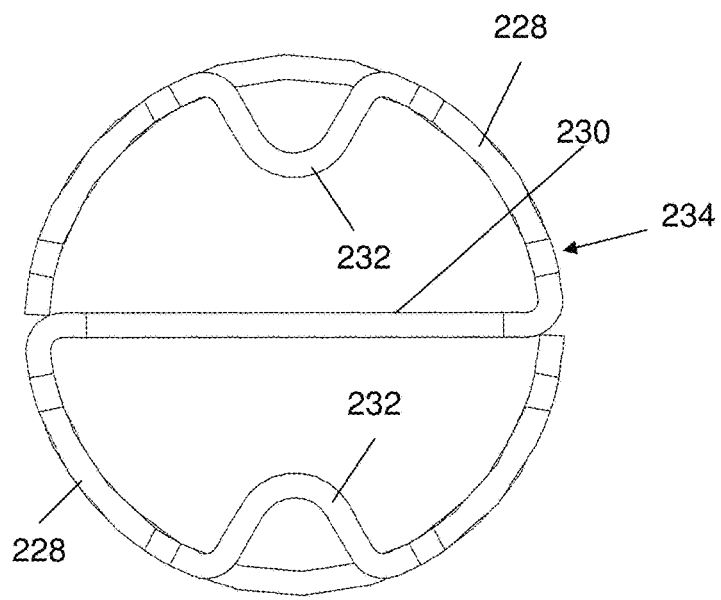
FIG. 17 schematically shows the shape of one link of FIG. 16.

FIG. 17 schematically shows the shape of one link 228. As can be seen link 234 is formed by bending projecting element 228 on one side of spine 230 upward into a semi-circular shape, while the projecting element 228 opposite the first one on the other side of spine 230 is bent downward into a semi-circular shape. The "free" ends of the projecting pieces can be welded to form a continuous perimeter or left unjoined as required by the application. In this embodiment, guides 232 for articulation cables are created in every third projecting element 228 as can be seen in the figures. The resulting shape in addition to guides 232 for articulation cables comprises open "windows" through which electrical and signal cables can be passed as well as working channels as needed by the application.

Figure 18A:
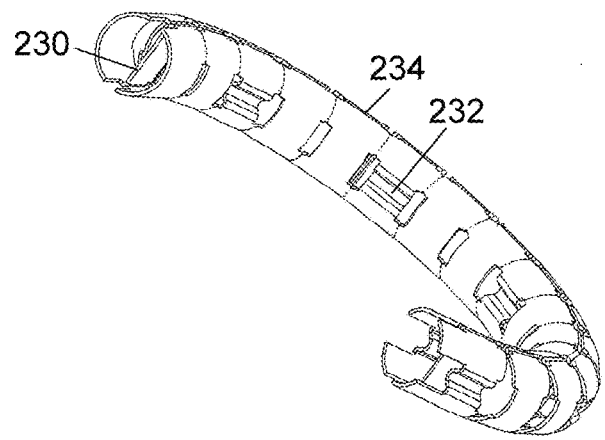
FIGS. 18A and 18B schematically show the entire articulation section of FIG. 16 in bent position and in straight position, respectively.
Figure 18B:
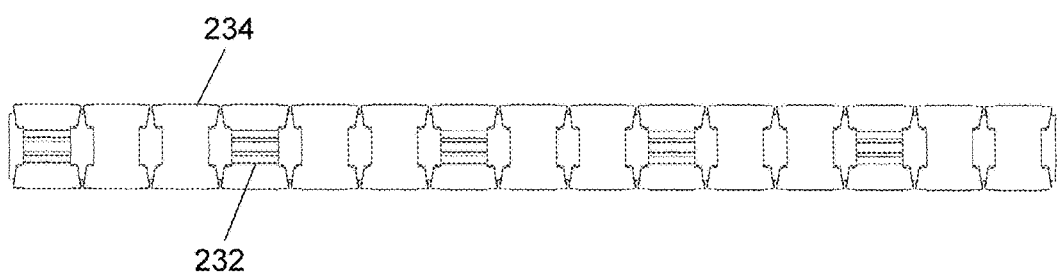
Figure 19A:
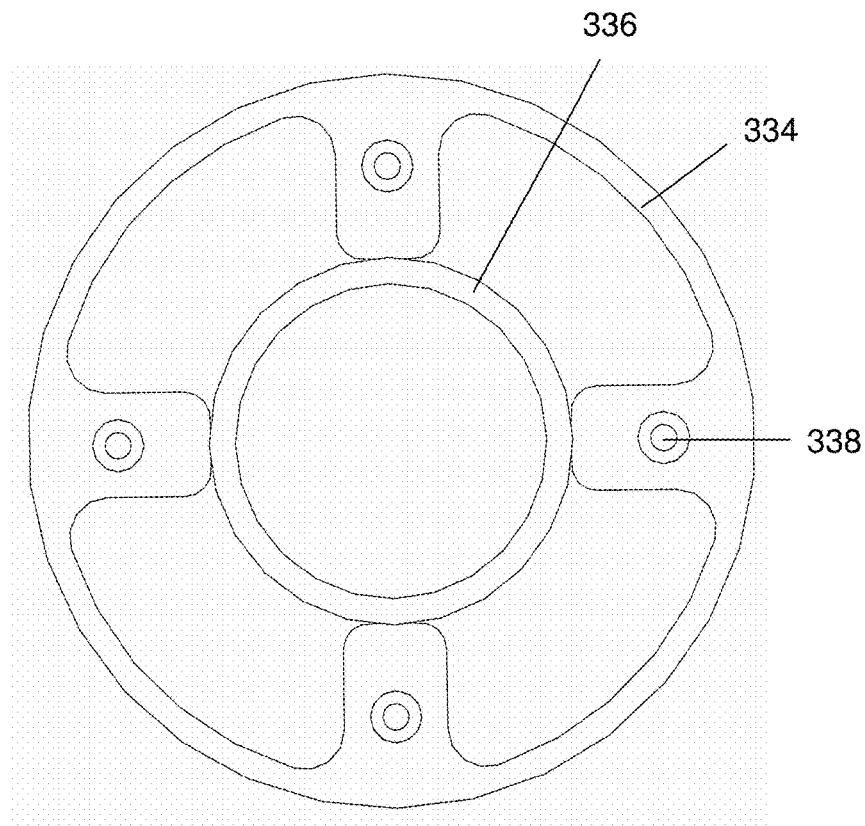
FIG. 19A and FIG. 19B schematically show an embodiment of articulation section comprised of individual vertebrae attached to an elongated axially located component of the probe.
Figure 19B:
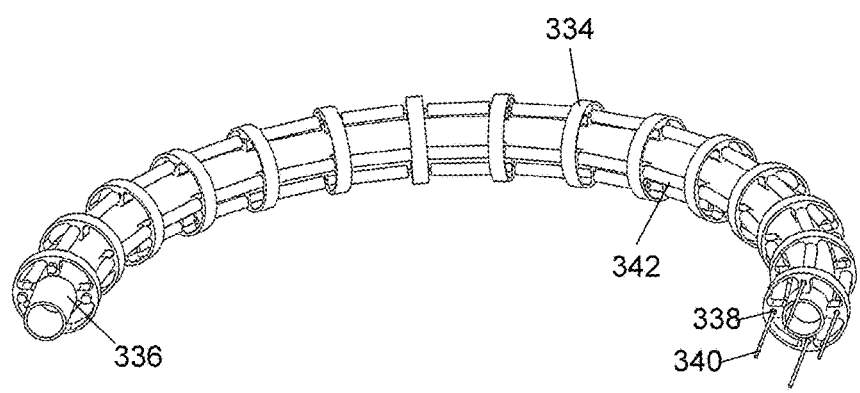

The entire bending section is seen—in bent configuration in FIG. 18A and in straight configuration in FIG. 18B. The typical dimension of a link according to the invention can be smaller than any other available link while maintaining the flexibility, minimum bending radius, rigidity and minimum length. For example, with 0.04 or 0.05 mm wall thickness, it is possible to construct different articulation sections starting from 1 mm diameter and up, different bending radiuses starting from 2 mm and up and different bending angles starting from zero (straight) and up to full angulations, i.e., 270 degrees in both directions. The minimum length of such articulation is the length of one link and it is in the range of 0.5 mm and up to 25 mm depending on the angulations and needed flexibility. Accordingly, the following conditions for the one piece articulation section are satisfied:
1 mm<Diameter of vertebrae<3 mm
2 mm<Bending radius<20 mm
Angulations angle ±270 degrees
0.04 mm<Wall thickens<0.5 mm
0.5 mm<Length of one link<25 mm FIG. 19A and FIG. 19B schematically show an embodiment of an articulation section comprised of a plurality of ring-shaped elements attached to an elongated flexible axially located component of the probe that passes through the center of each of the elements, thereby maintaining a predetermined distance between and acting as a hinge connecting adjacent elements. In this embodiment the individual elements 34, made of metal or plastic are shaped as shown in FIG. 19A. The elements 334 are attached by welding or gluing directly to a working channel 336, camera cable, or similar component that passes through the length of the probe. Elements 334 are provided with either two or four holes 338, through which articulation cables can pass allowing the articulation section to be bent in either two directions or four directions.

FIG. 19B shows a complete articulation section according to this embodiment. A plurality of elements 334 are attached to central working channel 336. Articulation cables 340 pass through holes 334 and sections of hollow tube 342 whose function it is to keep the articulation section from collapsing when the cables are pulled. An advantage of this embodiment of the articulation section is that the thin-walled working channel is always kept centered on the axis of the articulation section, thereby preventing the working channel from kinking during the bending process. The articulation section shown in FIG. 19B was designed for use in a 2.8 mm diameter single use probe.

Figure 20A:
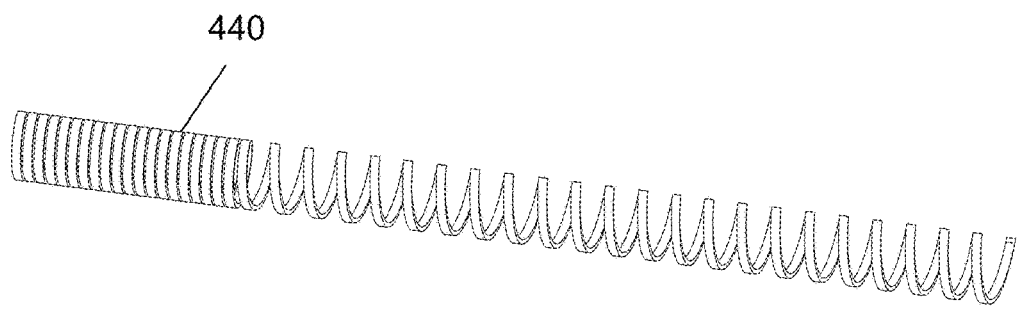
FIG. 20A-FIG. 20D schematically show another embodiment of a vertebrae section suitable for use with the small diameter probes of the invention.

FIG. 20A-FIG. 20D schematically show another embodiment of a vertebrae section suitable for use with the small diameter probes of the invention. In this embodiment the entire insertion section is made of a single metallic, e.g. stainless steel or nitinol, spring 440 that is covered with the conventional rubber tube (not shown in the figures). Near the distal end of spring an articulation section is created by stretching a portion of the spring to create space between adjacent coils as shown in FIG. 20A.

Figure 20B:
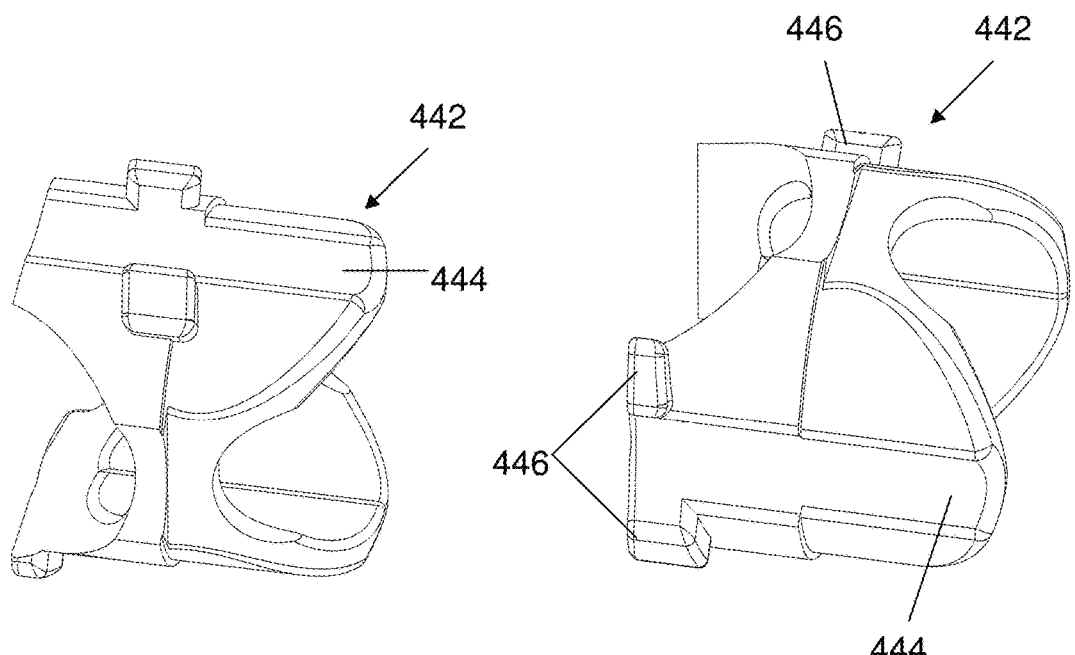
Figure 20C:
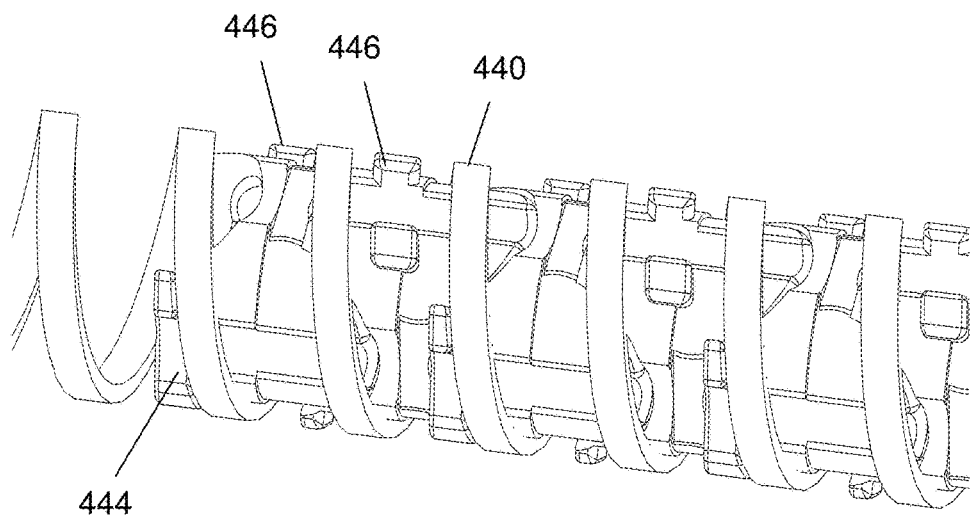
Figure 20D:
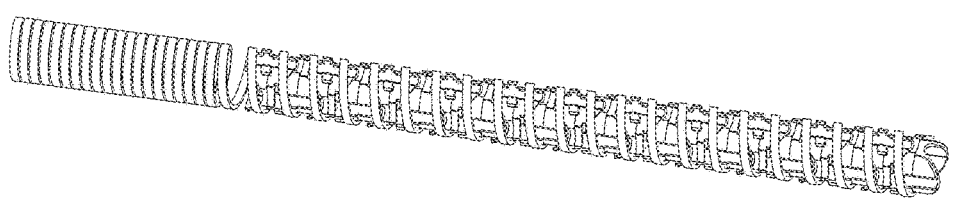

FIG. 20B shows two plastic inserts 442 that are "screwed" into the distal end of the spring to act as vertebrae and to prevent the distal end of the spring from becoming irreversibly kinked when bent. As seen in FIG. 20B, inserts 442 have longitudinal cable guides 444 created on the outer surface; four radial projections 446 on the outer surface, which fit between the coils of spring 440 (as shown in enlarged view in FIG. 20C) to keep adjacent inserts 442 from separating when the articulation section is bent; and two roughly semicircular projections on one end and two matching roughly semicircular recesses oriented at 90 degrees to the projections on the other end. Adjacent inserts 442 are rotated 90 degrees with respect to each other when the vertebrae section is assembled such that the projections on one insert enter the recesses on the neighboring insert to provide the surfaces around which the inserts/vertebrae pivot when the articulation section is bent.

FIG. 20E shows the fully assembled articulation section with the rubber covering removed. The length of the proximal end of the spring relative to the distal end, i.e. the articulation section, will in most instances be much longer than shown and will be equal to the length of the insertion section of the probe. Depending on if two or four bending cables are used, this embodiment of articulation section can be adapted for either two-way or four-way bending.

Another aspect that must be considered when designing miniature probes is the length and diameter of the tip, i.e., the distal part of any surgical/endoscopic tool/device. Due to anatomical constrains one of the basic requirements of any endoscopic tool that enters a cavity (natural or not) is to cause minimum trauma if any at all. There are many cases where the first part, i.e., the tip of the tool must be as short as possible in order not to injure the organ or for smooth passage through the organ. For example, the common bile duct has a constraint that a rigid length over 8 mm might cause an injury. Lengths over 10 mm are dangerous. In another case, for example in the kidney, 7 mm is considered as a maximum rigid length of a tip.

Using the above described 0.7 mm×0.7 mm CMOS sensor, a LED with 0.625 mm×0.285 mm dimensions, and different diameters for working channels or irrigation/insufflations tubes, yields the minimal diameter distal tip. In order to further reduce the diameter of the distal tip, it is possible to use an array of microLEDs having different shapes and to fill the empty area on the distal tip more efficiently. The typical maximum dimension of a microLed is 15- to 50 micron.

Figure 21:
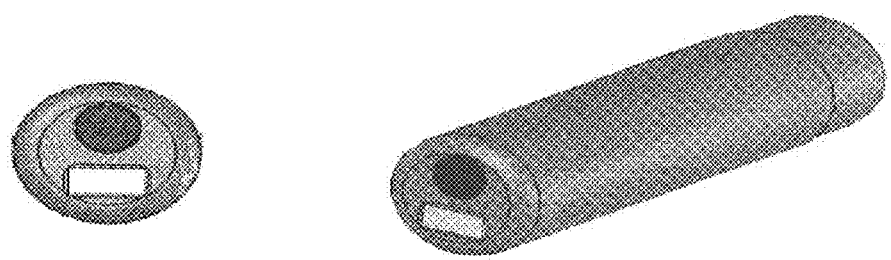
FIG. 21 is an example of the tip of a device according to the invention, with camera and LED, VCSEL, or MicroLED array illumination, diameter 1.51 mm and 3 mm length.

One example of a distal tip, with camera head and LED, VCSEL, or MicroLED array illumination, that has diameter 1.51 mm and 3 mm length, is shown in front and side views in FIG. 21.

Figure 22:
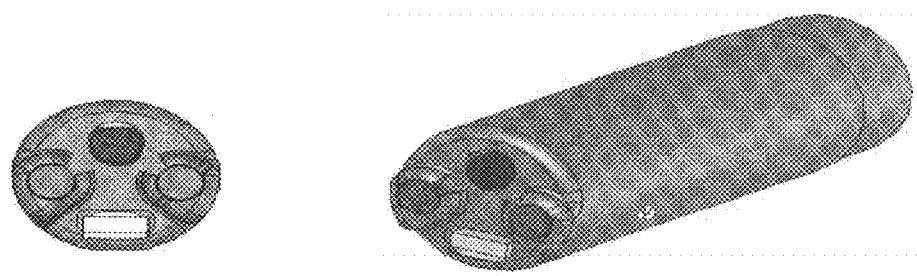
FIG. 22 is an example of the tip of another device according to the invention, with a tip with 1.99 mm diameter and 4 mm length that contains a camera, LED, and irrigation channel.

Another example of a distal tip with 1.99 mm diameter and 4 mm length that contains a camera head, a LED, VCSEL, or MicroLED array, an insufflation channel and an irrigation channel, is shown in front and side views in FIG. 22.

Figure 23:
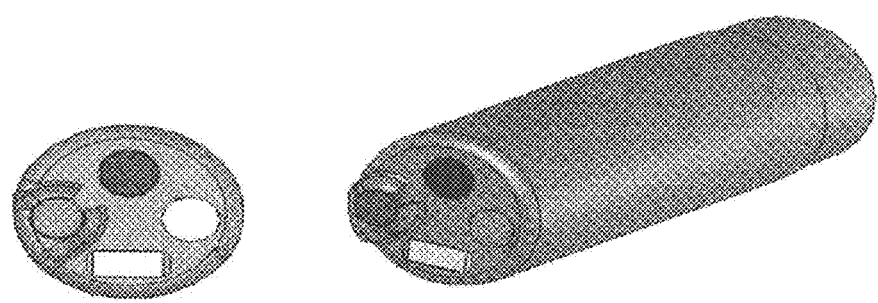
FIG. 23 is an example of the tip of another device according to the invention, with a tip with 1.99 mm diameter and 4 mm length a different combination of LED, VCSEL, or MicroLED array, irrigation and an empty working channel that can be used for advancing other tools.

A third example of a distal tip with 1.99 mm diameter and 4 mm length that contains a camera head, LED, VCSEL, or MicroLED array, irrigation channel, and an empty working channel that can be used for advancing other tools or for an additional fixed accessory such as a balloon, forceps, ultrasound, etc., that need an electrical cable for feeding this accessory, is shown in front and side views in FIG. 23.

Figure 24A:
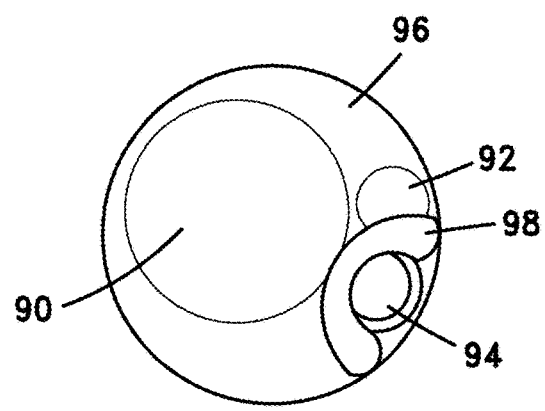
FIGS. 24A and 24B show an example of a distal tip of a 1.75 mm angioscopy catheter provided with a convex cover.
Figure 24B:
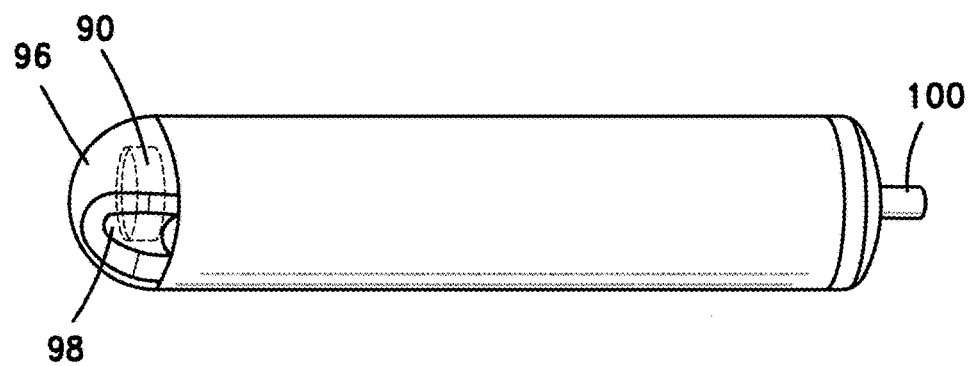

A fourth example of a distal tip is shown in FIGS. 24A and 24B. This distal tip is attached to a catheter used for performing angioscopy procedures. FIG. 24A is a frontal view in which can be seen the camera head 90, source of illumination 92, and a working channel 94. As best seen in the side view of FIG. 24B, the distal end is covered by a transparent convex, e.g. hemispherical, cover 96 to prevent damage to the lumen as the catheter is advanced. Cover 96 has an opening 98 over the working channel. At the proximal end of the tip is an electrical cable connector 100. The maximum outside diameter of cover 96 is equal or less than the maximum outside diameter pf the distal tip. The sensor is the 0.7 mm×0.7 mm sensor described herein above. The diameter of the camera head 90 is 1.1 mm. The illumination source can be either an optical fiber or LED having a diameter of 0.25 mm or an array of MicroLEDs. The working channel has a diameter of 0.3 mm and the overall diameter of the tip is 1.75 mm and its length in different embodiments is between 2.5 mm and 4 mm.

Using a smaller sensor, such as 0.5 mm×0.5 mm and smaller LED, VCSEL, or MicroLED array will make it possible to reduce the diameter of the distal tip by an additional 0.3 mm.

The above examples satisfy the following conditions
1.0 mm<Tip's Diameter<2.8 mm
2.5 mm<Tip's Length<4 mm The main problem of reducing the overall length of the tip of the tool can be looked upon as having to solve the individual problems of reducing the lengths of the components involved in the construction of such tool. For example, in an endoscopic tool, the tip will contain the following elements: solid state imager, optical objective, electronics, cable, housing, etc. The solid state imager and the objective affect the overall length of the tip. Therefore, reduction in the length of these components will directly reduce the tip's length. One option is to eliminate the package for the SSI. This will reduce the size in case of BGA packages or wafer level packages (WLP). The other option is to use through hole silicon vias (TSV), as described herein above, and to connect them directly to the cable used to bring power to the SSI and signals to and from it. A further option is to use direct wire bonding from the imager's pads to the cable (with or without an interim layer), as further illustrated in FIG. 6.

Figure 6:
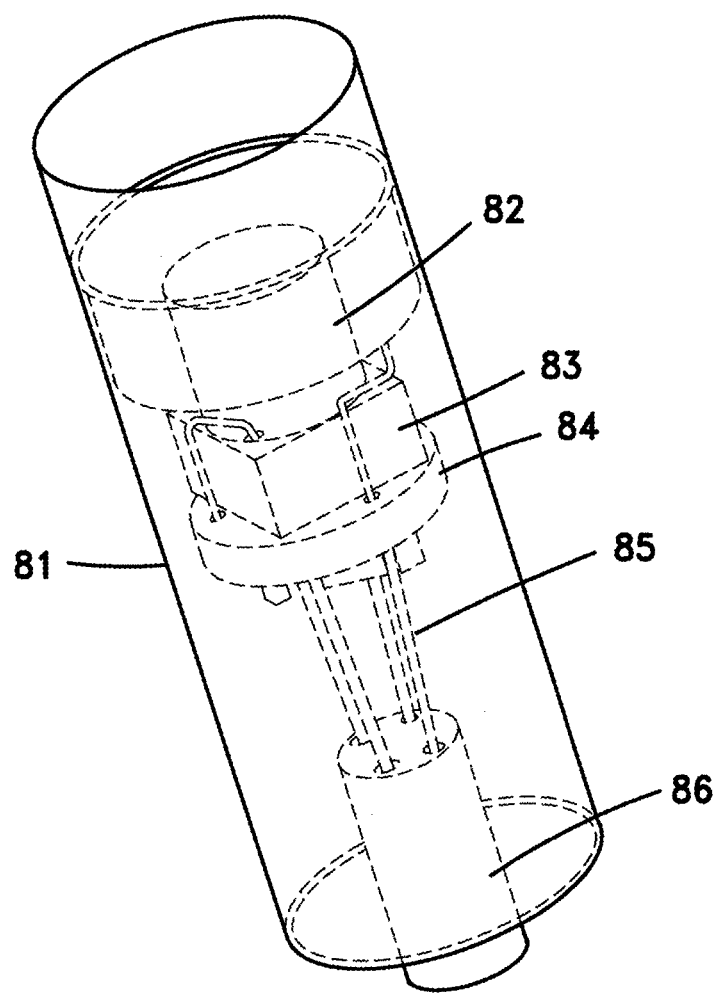
FIG. 6 illustrates the direct wire bonding from the imager's pads to the cable (with or without interim layer)

FIG. 6 schematically shows the distal tip of an endoscope according the invention. Part of the outer covering 81 of the distal tip has been removed to reveal the interior. Inside the cover 81 are located an optical assembly 82 mounted in front of sensor 83. In the embodiment shown, the sensor is wire bonded to electrical contact pads on a support layer 84. In this case it is also possible to mount components of a small driver on support layer 84. Through vias are used to electrically connect the top of support layer 84 to its bottom and to wires 85 of cable 86 that conducts power and electrical signals from the distal tip to the proximal end of the endoscope.

Another option for shortening the height, i.e. front to back distance, of the sensor is to eliminate the glass that covers the pixel (and microlenses) and to use a polymer solution to cover the pixels. As an example, it is possible to use a few microns of top coat polymer, which reduces the height of the sensor (and therefore the length of the distal tip by 0.05 to 0.5 mm.

Another object of the invention is to reduce the objective length. This task must be undertaken while taking into consideration the requirements of the optical performance (MTF, depth of field, distortion, etc.). For example, in order to satisfy a large field of view under certain illumination conditions and using spherical lenses, the objective must include an iris. A mechanical iris has a certain length and the solution of this problem has to be provided. One way of eliminating the mechanical iris is to create an iris by metalizing one surface of one lens and etching the iris therein. This essentially eliminates the dimension of the iris. Examples of such a design that satisfies the conditions of objective length smaller than 2.2 mm or 1.5 mm with their corresponding optical MTF (modulation transfer function), are described in detail below. The same principle can be applied to IR filters by implementing the filter as a coating on one of lens surfaces. Employing these methods results in a complete objective lens system that can be smaller in length than 3 mm using spherical lenses having a FOV (field of view) of 100 degrees. It also possible to show (based on the same argument) that with a FOV of 80 degrees it is possible to reduce the length to 1.5 mm and systems having a larger FOV can be built with only a slightly longer length.

The matter however is different when using a-spherical lens. In this case it is possible to show that for a FOV smaller than 80 degrees, the length of the tip is less than 2.5 mm and for a large FOV less than 4 mm. All of these tips can be implemented with one or two a-spherical lenses.

Figure 1A:
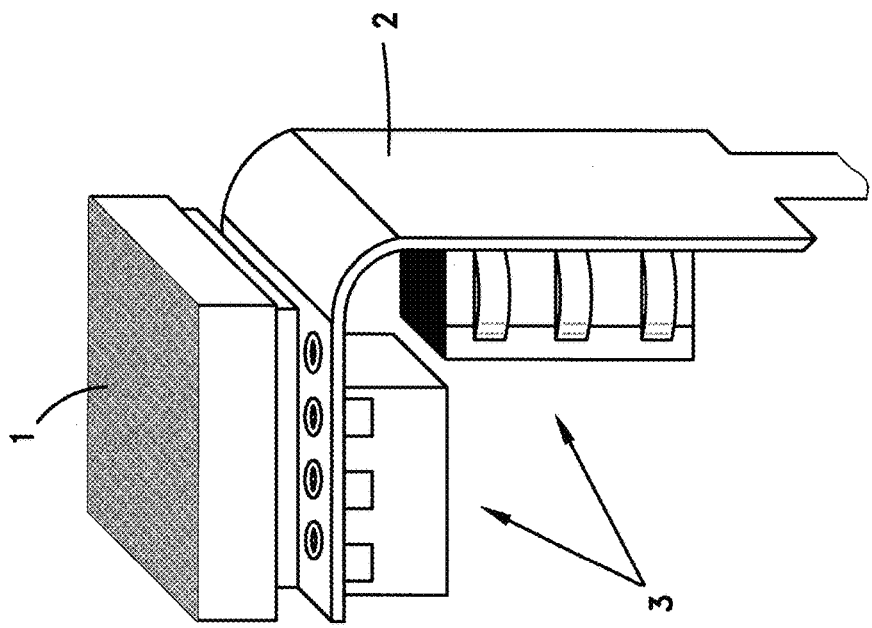
FIG. 1A schematically illustrates the assembly of the Solid state imager and electronics used in the manufacturing of the probe according to one embodiment of the invention.

Looking now at FIG. 1A, a CMOS chip 1 is supported on PCB 2 which comprises electronics generally indicated at 3. When assembled, the imaging CMOS assembly assumes a compact form, as seen in FIG. 1B, with connectors 4 through which signals generated by CMOS 1 can be transmitted to other image processing apparatus. Also seen in FIG. 1B is glass cover plate 5, which as mentioned herein above is not needed.

Compact configurations of this type, with and without PCBs, are disclosed in detail in WO2005/002210 and WO 2005/115221 of the same applicant hereof. The manufacturing of these assemblies are therefore not discussed herein in detail, for the sake of brevity.

FIG. 2A to FIG. 2E schematically show various views of the optical assembly 20, which is shown coupled to CMOS 1 in FIG. 2A.

Figure 2F:
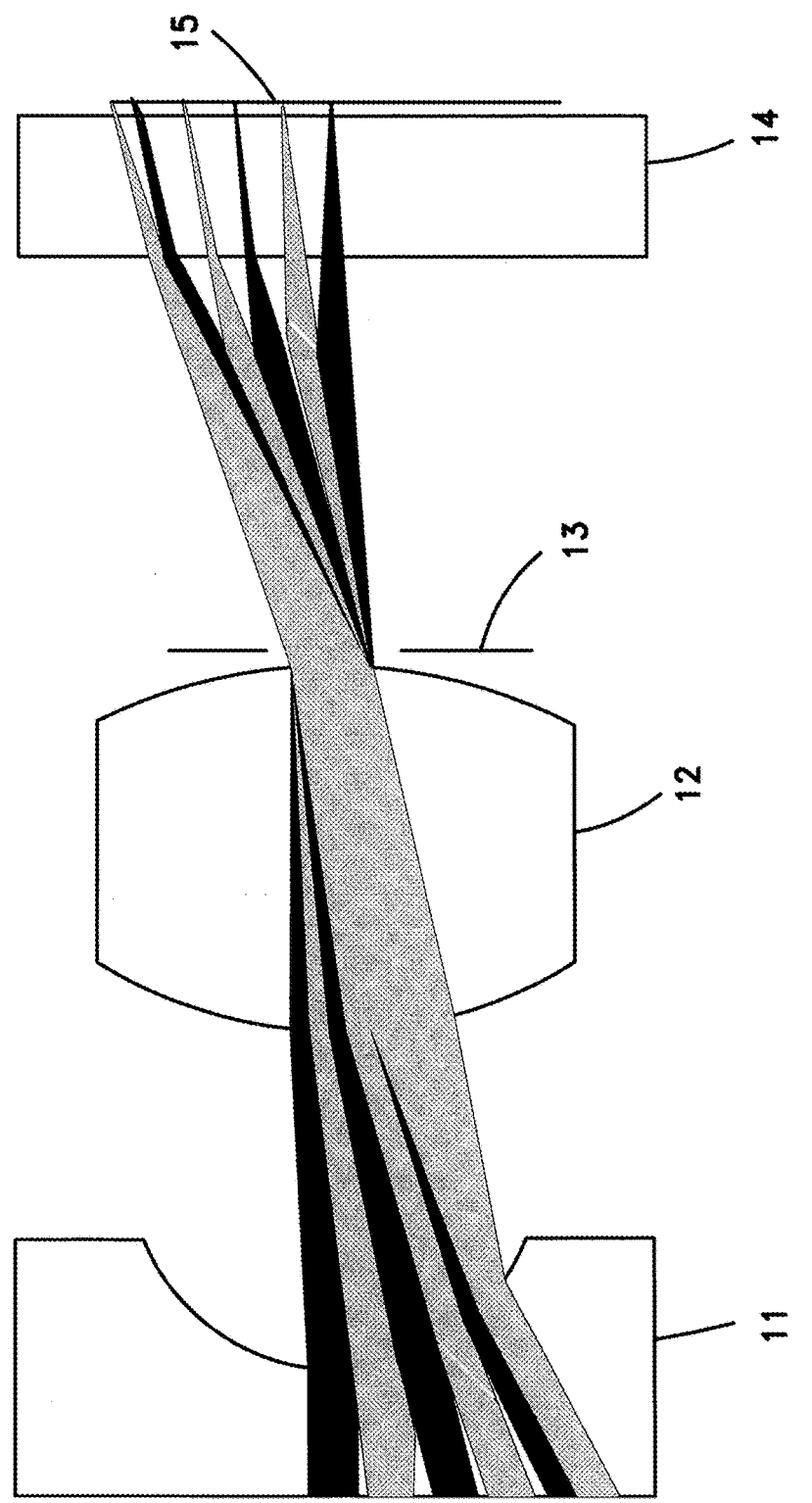
FIG. 2F shows the lens layout of the optical assembly of FIG. 2A.

The lens layout of optical assembly 20 is shown in FIG. 2F. The lens assembly 20 comprises two lenses both of which are made from glass or polymer. In FIG. 2F, 11 is Lens 1, 12 is Lens 2, 13 is the iris, 14 is the CMOS cover glass, and 15 is the CMOS active area.

Figure 9:
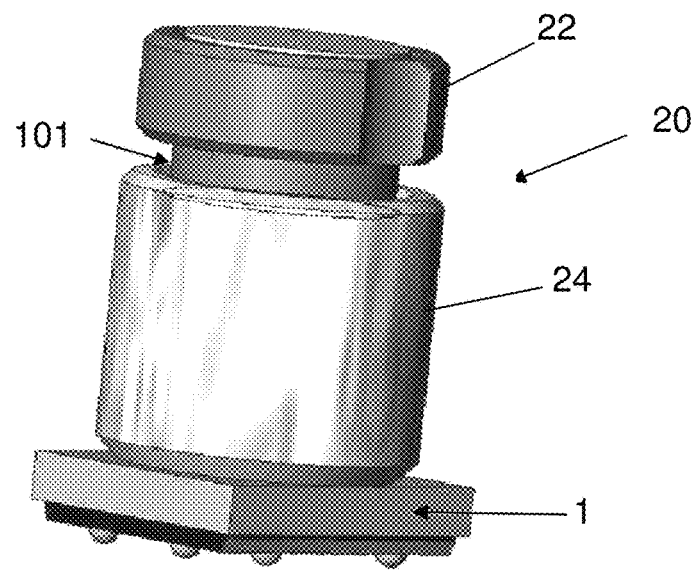
FIG. 9 schematically illustrates the mechanical parts of an embodiment of a CMOS optical assembly.
Figure 10:
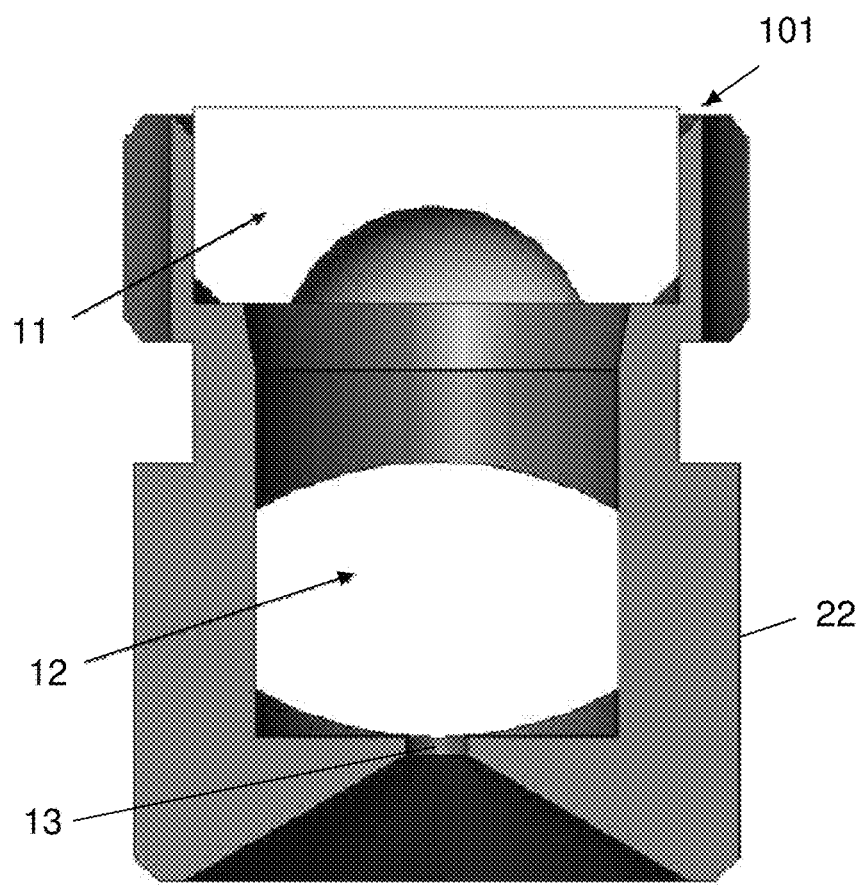
FIG. 10 shows the structure of the CMOS optical assembly of FIG. 9 in cross section.

The opto-mechanical elements of the optical assembly 20 in this example are shown in FIG. 9. They comprise three parts: main tube 22, CMOS holder 24, and CMOS chip 1, including its cover glass. FIG. 10 is a cross-sectional view of lens assembly 20 from FIG. 9 showing the optical components, which are also shown in FIG. 2F. The lenses of the optical assembly are assembled in the main tube 22 in the following order: First, mechanical iris 13 is inserted inside the main tube followed by Lens 2 (numeral 12). Next, Lens 1 (numeral 11) is positioned at the front of the main tube 22. Lens 1 is sealed to tube 22 by glue, such as Glue EPOTEK 353 or a UV epoxy, indicated by numeral 101, to avoid penetration of water during an endoscopic procedure. After that, a CMOS holder 24 is glued onto the cover glass of the CMOS chip 1. The CMOS holder 24 is then screwed onto the main tube 22 for focus adjustment. Finally, the optical assembly 20 is sealed by glue.

As previously discussed, one of the objectives of the invention is to minimize the length of the objective lens in the camera head. The following discussion of techniques for minimizing the length of the objective lens is made with reference to spherical lenses. Obviously with a-spherical lenses the solution is simpler since it is possible to reduce the number of optical elements hence to effectively reduce the entire objective length.

The optical design of a complete objective takes into account several parameters, for example: the Field Of View (FOV), the Depth of Field WOO, the pixel dimension, the effective area of the sensor, and the orientation of its optical axis in comparison to the mechanical axis of the entire solid state sensor camera head. For the sake of simplicity of this description, it is assumed that these two axes coincide; if they do not coincide, a shift in mechanical part and/or assembly must be considered, or in case of aspherical lenses the mould for the lenses can take this shift into consideration. Other parameters also affect the design, for example the level of distortion and F number. If the distortion is too high, then a 'fish eye' effect appears and if the F number is too high, more illumination is needed to receive a bright image.

In the following example is demonstrated a short optics system with 100 degrees FOV for a 0.7 mm×0.7 mm solid state sensor with effective area of 492µ×492µ and F/3.5 system that satisfies the condition: length of objective from the surface of sensor 8 to the front surface of first lens 6 is less than 2.05 mm. The optical system comprised of a triplet first lens 6 and doublet second lens 7 is shown in FIG. 7A. The diameter of all of the optical elements is 0.8 mm.

Figure 7C:
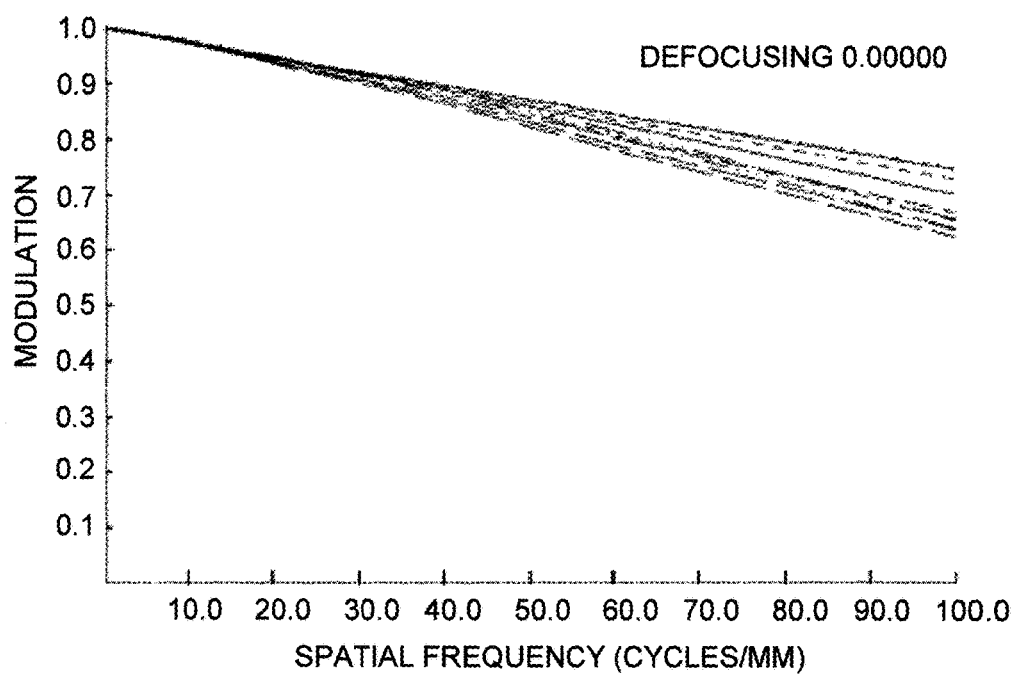
FIG. 7C shows the Modulation Transfer Function of the lens assembly of FIG. 7B.

The FOV of the system shown in FIG. 7A can be increased to 140 degrees by changing the design of the first element in first lens 6 as shown in FIG. 7B. The system shown in FIG. 7B has an F-number of F/2.5 and length of 2.14 mm. All other dimensions of the optical element and sensor are the same. FIG. 7C shows the Modulation Transfer Function of the optical system of FIG. 7B.

In order to reduce the number of mechanical elements—since in such dimension it is almost impossible to produce a very accurate mechanical iris (with accuracy of several microns)—a different method of implementing the iris is used. One of the lenses, in this case a plano lens with minimal thickness is used to implement an iris by metalizing one surface and etching the iris on the surface with very high accuracy. It is also possible to use the other surface of the lens and also to implement an IR rejecting filter by using a coating process on the surfaces of one of the lenses.

Figure 8:
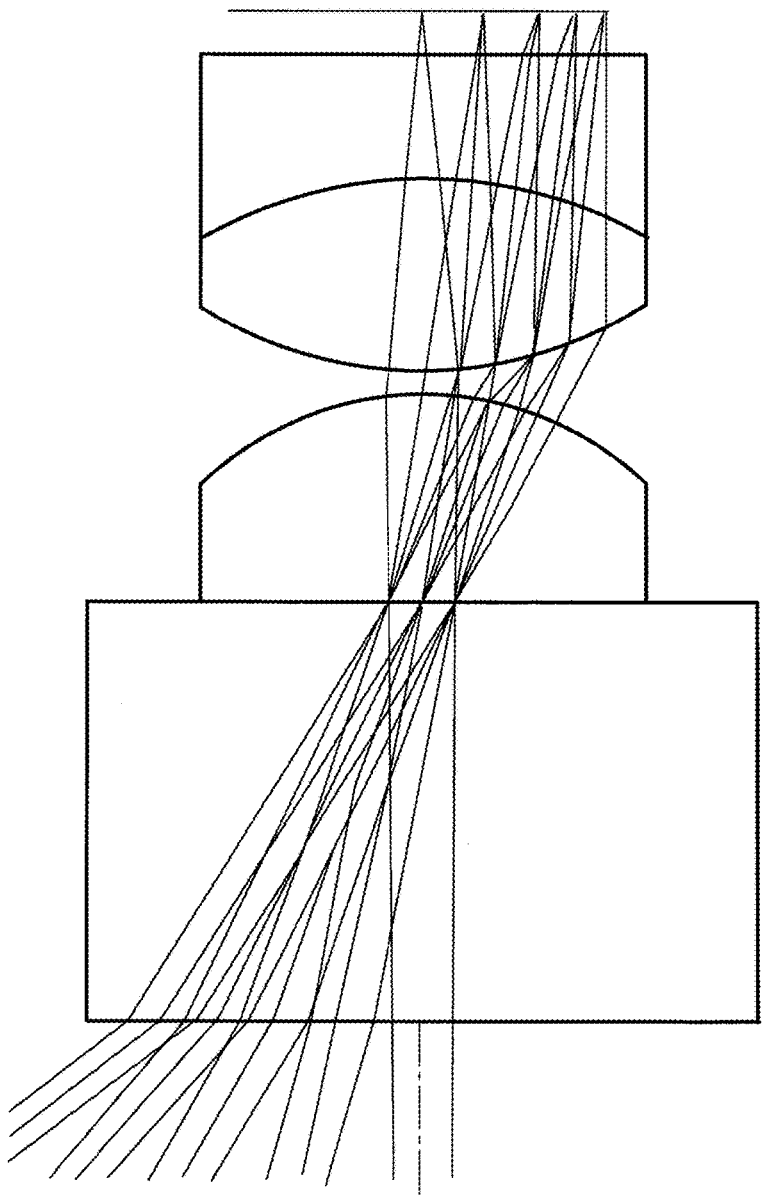
FIG. 8 illustrates a length of objective from sensor surface to first lens <1.96 mm.

Obviously it is possible to use the plano lens as a filter and to implement the metallization and etching process to create the iris on one surface, as illustrated with reference to FIG. 8 for the same parameters as before, but with the length of the objective satisfying the condition: length of objective from sensor surface to first lens is less than 1.96 mm. In this case the plano filter is made from Schott Glasses material BG40.

Figure 13:
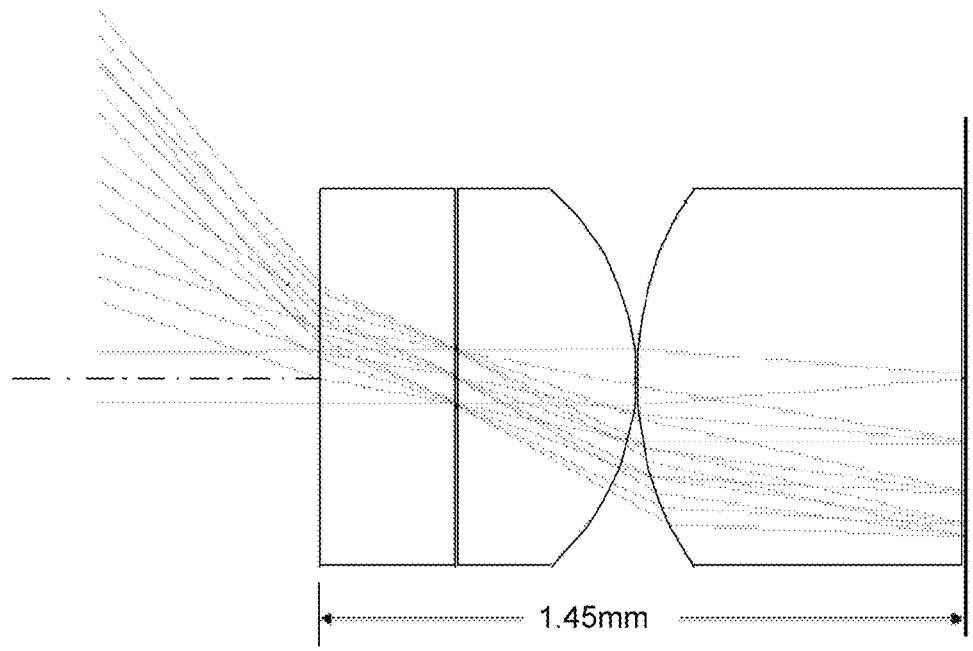
FIG. 13 illustrates the optimization of the length, by reducing the number of lenses.

In order to further optimize the length, it is possible to reduce the number of lenses, as shown in FIG. 13. In this case the same parameters as in the previous example are used, except for F/4. In this example, the length of the objective satisfies the condition: length of objective from sensor surface to first lens is less than 1.45 mm. In addition, in this case the lens is directly glued (cemented) over the solid state imager.

Figure 14:
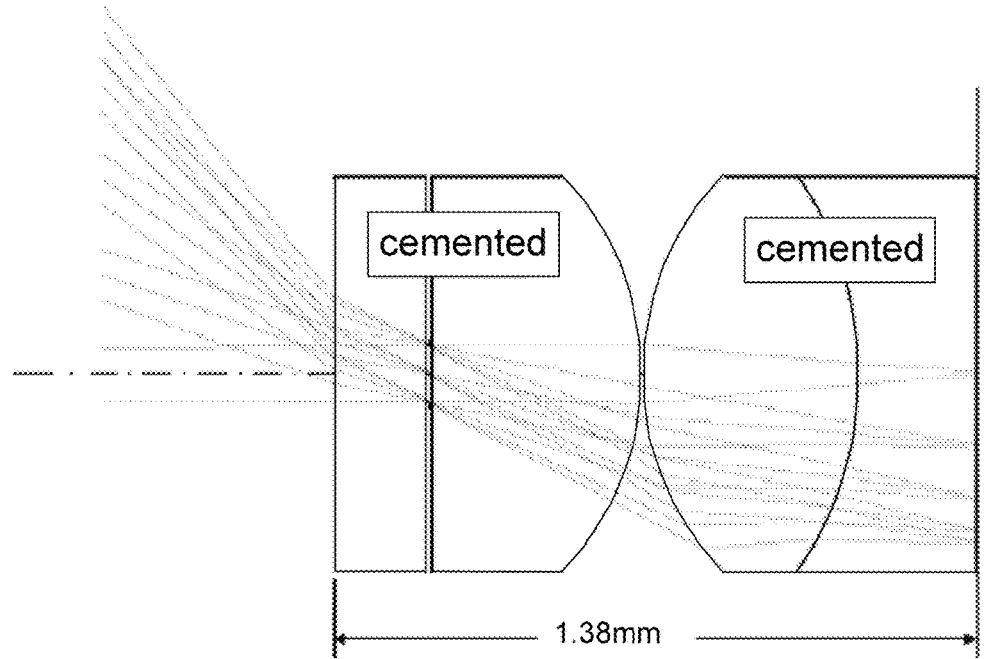
FIG. 14 illustrates a further reduction of the length by constructing one of the lenses in FIG. 13 from a doublet.

Another embodiment of the lens glued to the SSI, i.e., constructing it from a doublet, as shown in FIG. 14. This embodiment allows further reduction of the overall length and the lens assembly satisfies the condition: length of objective from sensor surface to first lens is less than 1.38 mm.

Figure 15:
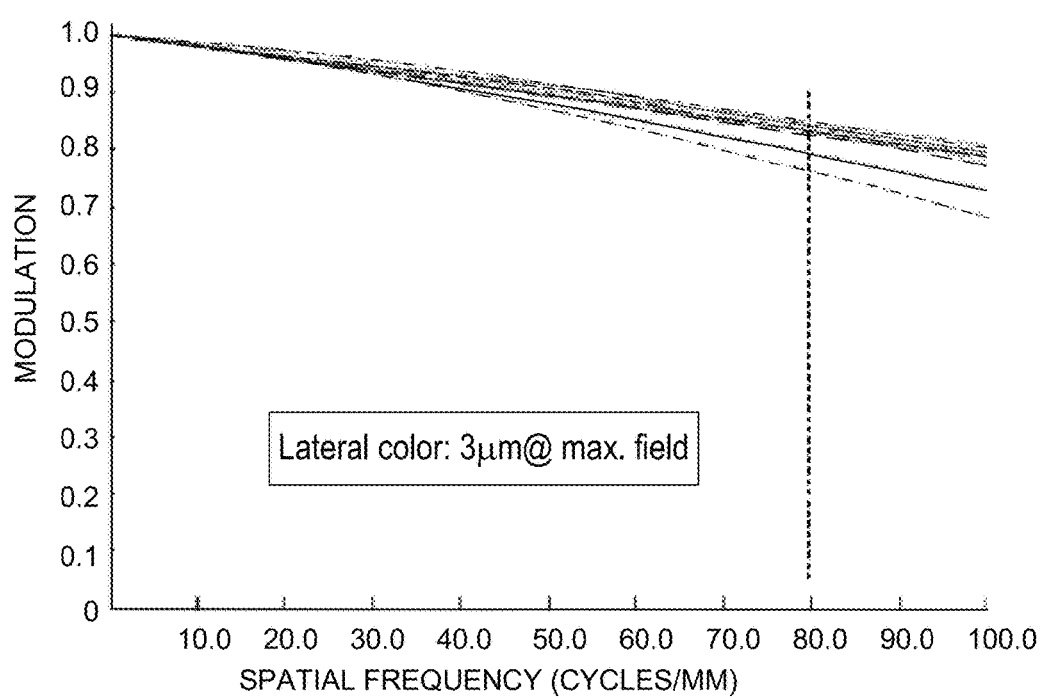
FIG. 15 shows the Modulation Transfer Function for the optical system of FIG. 14 having a length of objective from sensor surface to first lens <1.38 mm.
Figure 16:
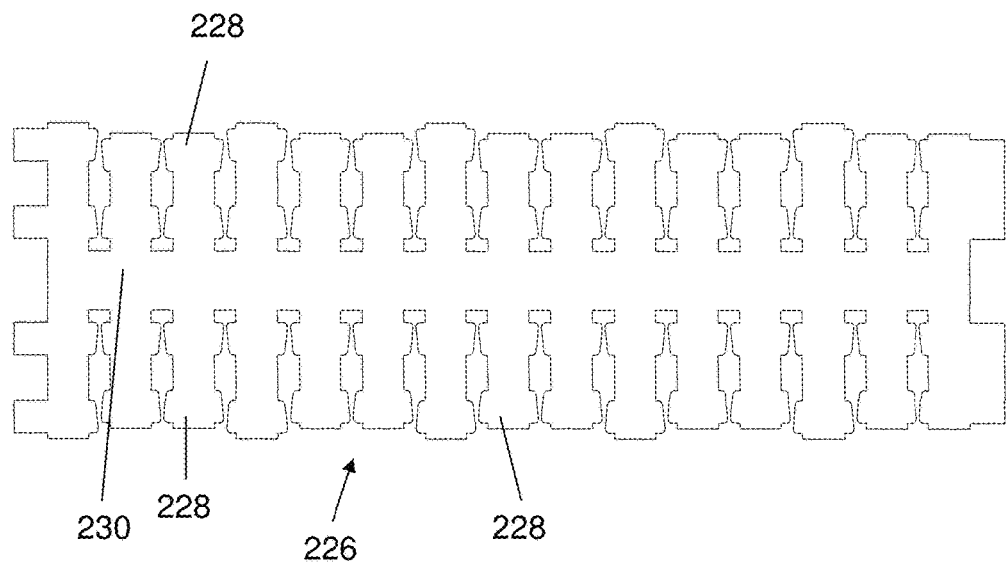
FIG. 16 illustrates a link and vertebrae of an articulation section according to the invention.

The resulting Modulation Transfer Function (MTF) for the lens system shown in FIG. 14 is shown in FIG. 15, where MTF satisfies the condition that MTF@80 pair lines/mm is greater than 0.78 for the visible band and MTF satisfies the condition that MTF@40 pair lines/mm is greater than 0.9 for the visible band.

In all the above examples, it has been demonstrated that eliminating the mechanical iris and implementing it as a metallization process over a lens and etching the "stop" or the hole" throughout to allow the rays to propagate to the solid state sensor created a short objective. Different designs of lenses have been presented herein as examples of the method and the MTF of the last system described was calculated. It was thereby demonstrating that the MTF of such a system is efficient and can serve in miniature video cameras based on solid state imagers. In addition, it has been demonstrated that for an objective lens system that meets the requirement of FOV>100 degress, the following parameters shown in Table 4 satisfy the minimum length of the objective:

TABLE 4

| Number of elements | Length of lens | Number of optical elements (doublet or triplet) |
| --- | --- | --- |
| 5 | 2.05 | 2 |
| 4 | 1.96 | 2 |
| 3 | 1.45 | 1 |
| 3 | 1.38 | 1 |

The same arguments and the same design concept apply to smaller FOV lens assemblies, for example 60 degrees or 80 degrees. In the case of 60 degrees FOV, the number of lens elements is reduced and it is easy to show that the number of elements can be 2 to 4 (depending on the level of MTF), while the maximum length of the objective is between 0.7 mm to 1.6 mm depending on the number of doublets used in the design. Also for the small FOV lens assemblies the concept of metallization and etching was used to construct the iris.

One final aspect of the invention is the construction of the camera heads, i.e. attaching the objective optic assemblies to the sensors. The photodiodes, microlenses, and sometimes associated electronics of the sensors are produced on silicon wafers using methods known in the art. The tops of the microlenses are then covered with either a transparent polymer layer or a cover glass. Then vias are drilled through the wafer, filled with conducting material and the ball grid assembly formed on the bottom of each sensor. The lens are then manually attached to the top of the sensors, either before or after the wafer is diced, as described with respect to FIG. 9 and FIG. 10 herein above.

Another much more efficient method of creating and attaching the objective lens assemblies to the sensors is the recently developed method known as wafer level optics (WLO). This method also affects the price of the entire camera by means of reducing the associated labor. In the WLO technology the lens are created by pressing a negative mold of the lens elements into a layer of transparent polymer spread onto a surface of a thin glass (or transparent polymer) substrate, removing the mold, and curing the polymer. Lenses can be created on one or both sides of the glass substrate and the exact thickness of the substrates and lens as well as the curvature and an optical axis shift if necessary of the lens elements is determined by the optical design as illustrated in the examples herein above.

The glass substrates are conveniently made in the same size and shape as the silicon wafers on which the sensors are created. The lens elements are created on the glass substrates at the exact locations of the sensors on the silicon wafers. After the lenses are cured, the glass substrates are stacked on top of the wafer using spacers as necessary to maintain the designed distance between lenses. Next the wafer and glass substrates are carefully aligned and bonded together using epoxy or any other method known in the art. Finally the wafers are diced to produce approximately 40,000 0.7 mm×0.7 mm camera heads from a single eight inch silicon wafer.

Figure 26A:
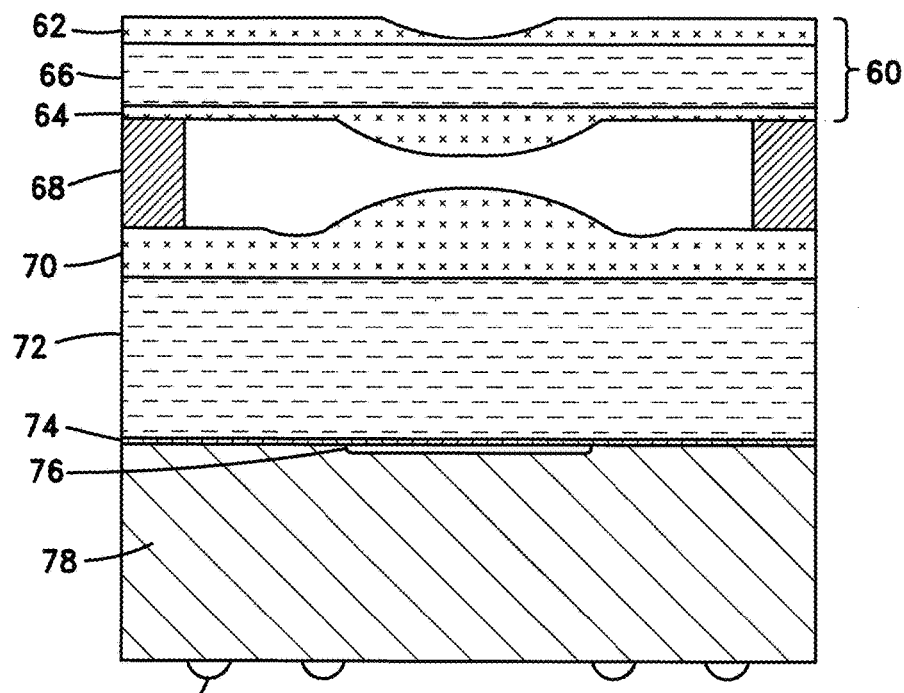
FIG. 26A schematically shows a cross sectional view of a completed camera head produced using the wafer level optics method.
Figure 26B:
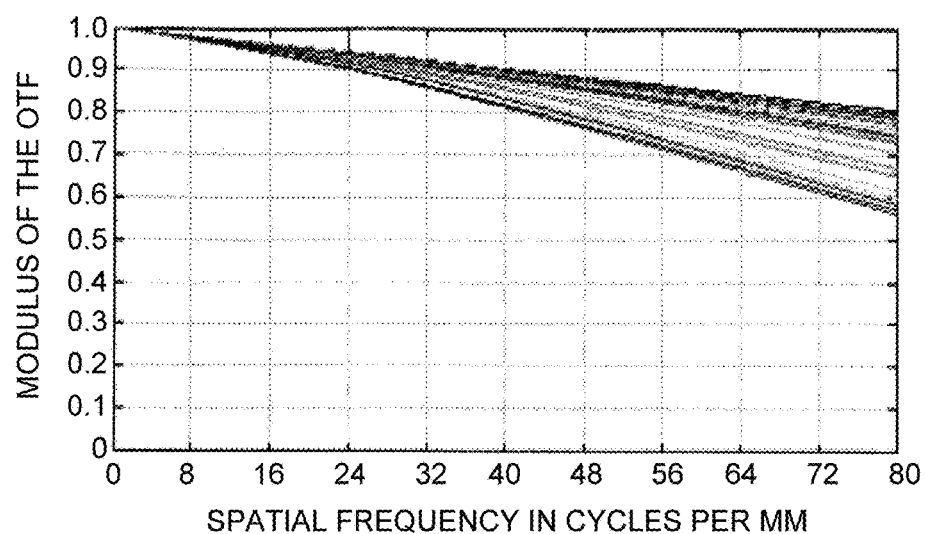
FIG. 26B shows the Modulation Transfer Function of the camera head of FIG. 26A.

FIG. 26A schematically shows a cross sectional view of a completed camera head produced using the wafer level optics method. Seen in this figure are first lens 60 comprised of lens elements 62 and 64 created on opposite surfaces of glass substrate 66, spacer 68, second lens element 70 created on glass substrate 72, epoxy and topcoat layer 74, pixel active layer 76 at the upper surface of silicon 78, and the ball grid assembly 80. The camera head shown in FIG. 26A has a diameter=1.1 mm, F number=F/3.5, and Field of View=140 degrees. The MTF of the camera head of FIG. 26A is shown in FIG. 26B.

The objectives of the invention, i.e. to produce very small size camera heads and disposable visualization probes that contain them, have been attained by utilizing the techniques described herein above, e.g. using a current methodology of the output video signal of the imager, through silicon vias, back side illumination pixel structures, and wafer level optics. Additionally the combination of these techniques allows the sub-millimeter camera heads to be produced in large quantities and at a low cost.

As will be apparent to the skilled person all the above description and examples have been provided for the purpose of illustration and are not intended to limit the invention in any way. The sub-millimeter probes of the invention can be employed to create many different surgical tools, and many such different tools can be created, which comprise sockets adapted to receive probes, according to the invention, at various locations as appropriate and convenient according to the different tools and procedures employing them. Accordingly, the invention opens the door for a new generation of medical devices in particular medical devices having diameters of 3.2 mm or less, without limitation to their shape, location of the probes and their intended use. It is also possible to "install" the probe without housing or to install a probe that already contains a housing in the tool.

We claim:

1. A video camera head comprising an objective lens assembly and a CMOS sensor;
    wherein the CMOS sensor comprises an array of photosensitive elements and electronics adapted to deal with the output signals of the photosensitive elements the electronics implemented together with the array of photosensitive elements on a silicon substrate and in that the silicon substrate comprises no more than two, three, or four electrical connecting pads configured to allow video signals to be sent from the electronics and power to be supplied to the electronics.

2. The video camera head of claim 1, wherein the objective lens assembly is implemented using wafer level technology.

3. The video camera head of claim 1, wherein the output video signal is carried by an electric current.

4. The video camera head of claim 1, wherein the video camera head has a maximum outer diameter of 1.4 mm or less.

5. The video camera head of claim 1, wherein the electrical connections between the electrically connecting pads and the solid state pick up device are implemented by means of through silicon vias.

6. The video camera head of claim 1, wherein the photosensitive elements of the solid state pick up device are implemented using back side illumination technology.

7. The video camera head of claim 1, wherein the length of the objective lens assembly is 2.5 mm or less.

8. The video camera head of claim 1, comprising an iris created by metalizing one surface of one lens of the objective lens assembly and etching the iris therein.

9. The video camera head of claim 6, comprising pixel cells having dimensions in the range of 2.2×2.2 microns to 0.9×0.9 microns.

10. A video camera head comprising a 0.7 mm×0.7 mm sensor and an integral 1.4 mm inner diameter light ring.

11. A visualization probe comprising illumination means, an objective lens assembly and a CMOS sensor;
    wherein the CMOS sensor comprises an array of photosensitive elements and electronics adapted to deal with the output signals of the photosensitive elements the electronics implemented together with the array of photosensitive elements on a silicon substrate and in that the silicon substrate comprises no more than two, three, or four electrical connecting pads configured to allow video signals to be sent from the electronics and power to be supplied to the electronics and wherein the visualization probe has a maximum outer diameter of 4 mm or less.

12. The visualization probe of claim 11, wherein the objective lens assembly is implemented using wafer level technology.

13. The visualization probe of claim 11, wherein the objective lens assembly is implemented using injection molded lenses.

14. The visualization probe of claim 11, wherein the output video signal is carried by an electric current.

15. The visualization probe of claim 11, wherein the electrical connections between the electrically connecting pads and the solid state pick up device and the integrated circuitry are implemented by means of through silicon vias.

16. The visualization probe of claim 11, wherein the photosensitive elements of the solid state pick up device are implemented using back side illumination technology.

17. The visualization probe of claim 11 comprising one or more of:
 a) an articulation section;
 b) a working channel.

18. The visualization probe of claim 17, wherein the articulation section is constructed without any hinges and in one piece.

19. The visualization probe of claim 18, wherein the articulation section is constructed from one plate, and in which each link is cut from the plate precisely by electromagnetic or mechanical apparatus to form a plurality of elements projecting outward from a spine and the projecting elements are then bent to form the individual vertebrae.

20. The visualization probe of claim 17, wherein the articulation section is constructed from a plurality of ring-shaped elements attached to an elongated flexible axially located component of the visualization probe/medical device, wherein the axially located component passes through the centers of the ring-shaped elements.

21. The visualization probe of claim 16 comprising pixel cells having dimensions that are in the range of 2.2×2.2 microns to 0.9×0.9 microns.

22. A medical device comprising a visualization probe comprised of illumination means, an objective lens assembly and a CMOS sensor;
 wherein the CMOS sensor comprises an array of photosensitive elements and electronics adapted to deal with the output signals of the photosensitive elements the electronics implemented together with the array of photosensitive elements on a silicon substrate and in that the silicon substrate comprises no more than two, three, or four electrical connecting pads configured to allow video signals to be sent from the electronics and power to be supplied to the electronics and wherein the medical device has a maximum outer diameter of 4 mm or less.

23. The medical device of claim 22, wherein the medical device is one of the following:
 a) an endoscope;
 b) a laparoscope;
 c) a guide wire;
 d) a flexible, semi-flexible, semi-rigid, or rigid single or multi-lumen tube;
 e) scissors;
 f) a scalpel;
 g) forceps;
 h) a spring;
 i) a rod;
 j) a device used for approximating tissues;
 k) a device used for cutting tissues;
 l) a device used for sealing tissues;
 m) a device for burning objects;
 n) a device for coagulating objects;
 o) a device for feeding;
 p) a device for guiding objects or substances to a location in a body;
 q) a device for draining objects or substances from a location in a lumen;
 r) a device for delivering objects or substances to a location in a lumen;
 s) a device comprising monitoring instruments or sensors;
 t) a device comprising diagnosis instruments or sensors; and
 u) a wireless in vivo device.

24. The medical device of claim 22 comprising one or more of:
 a) an articulation section;
 b) a working channel.

\* \* \* \* \*

(12) EX PARTE REEXAMINATION CERTIFICATE (242nd)
Ex Parte Reexamination Ordered under 35 U.S.C. 257

United States Patent
Sonnenschein et al.

(10) Number: US 10,188,275 C1
(45) Certificate Issued: Apr. 22, 2024

(54) SMALL DIAMETER VIDEO CAMERA HEADS AND VISUALIZATION PROBES AND MEDICAL DEVICES CONTAINING THEM

(71) Applicant: Medigus Ltd., Omer (IL)

(72) Inventors: Elazar Sonnenschein, Beer Sheva (IL); Ariel Smoliar, Rehovot (IL); Yuval Malka, Beer Sheva (IL)

(73) Assignee: SCOUTCAM LTD.

Supplemental Examination Request:
No. 96/000,417, Nov. 10, 2022

Reexamination Certificate for:
Patent No.: 10,188,275
Issued: Jan. 29, 2019
Appl. No.: 15/051,265
Filed: Feb. 23, 2016

Related U.S. Application Data

(63) Continuation of application No. 14/324,531, filed on Jul. 7, 2014, now abandoned, which is a
(Continued)

(51) Int. Cl.
| | |
|---|---|
| *A61B 17/29* | (2006.01) |
| *A61B 1/00* | (2006.01) |
| *A61B 1/005* | (2006.01) |
| *A61B 1/012* | (2006.01) |
| *A61B 1/05* | (2006.01) |
| *G02B 23/24* | (2006.01) |
| *H04N 5/374* | (2011.01) |
| *H04N 23/54* | (2023.01) |
| *H04N 23/55* | (2023.01) |
| *H04N 23/57* | (2023.01) |
| *H04N 25/76* | (2023.01) |
| *A61B 1/06* | (2006.01) |
| *A61B 17/22* | (2006.01) |

(Continued)

(52) U.S. Cl.
CPC ............ *A61B 1/05* (2013.01); *A61B 1/00096* (2013.01); *A61B 1/0055* (2013.01); *A61B 1/012* (2013.01); *A61B 1/051* (2013.01); *A61B 17/29* (2013.01); *G02B 23/243* (2013.01); *H04N 23/54* (2023.01); *H04N 23/55* (2023.01); *H04N 23/57* (2023.01); *H04N 25/76* (2023.01); *A61B 1/0684* (2013.01); *A61B 2017/22042* (2013.01); *A61B 2090/306* (2016.02); *A61B 90/361* (2016.02); *H01L 27/14621* (2013.01); *H01L 27/14645* (2013.01); *H04N 23/555* (2023.01)

(58) Field of Classification Search
None
See application file for complete search history.

(56) References Cited

To view the complete listing of prior art documents cited during the supplemental examination proceeding and the resulting reexamination proceeding for Control Number 96/000,417, please refer to the USPTO's Patent Electronic System.

*Primary Examiner* — Matthew E Heneghan

(57) ABSTRACT

In a first aspect the invention is a video camera head comprising an objective lens assembly and a solid state imager (SSI) comprised of a solid state pick up device and integrated circuitry adapted to produce an output video signal. The SSI is configured to allow video signals to be sent from the SSI and power to be supplied to the SSI by means of four or less electrically connecting pads. In a second aspect the invention is a video camera head comprising a 0.7 mm×0.7 mm sensor and an integral 1.4 mm inner diameter light ring. In a third aspect the invention is a visualization probe comprising illumination means and a video camera head of the first aspect. The visualization probe has a maximum outer diameter of 2.8 mm or less. In a fourth aspect the invention is a medical device comprising a visualization probe of the third aspect. The medical device has a maximum outer diameter of 3.2 mm or less.

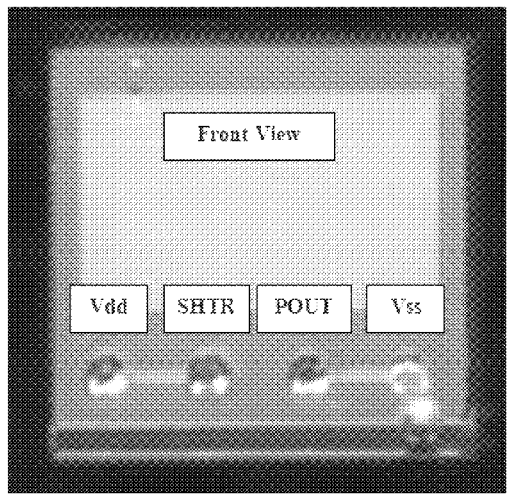

Related U.S. Application Data continuation-in-part of application No. 12/883,288, filed on Sep. 16, 2010, now Pat. No. 8,803,960.

(60) Provisional application No. 61/242,823, filed on Sep. 16, 2009.

(51) Int. Cl.
*A61B 90/00* (2016.01)
*A61B 90/30* (2016.01)
*H01L 27/146* (2006.01)
*H04N 23/50* (2023.01)

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 4-9, 11, 15, 16, 20 and 22 are determined to be patentable as amended.

Claims 2, 3, 12-14, 17-19, 21, 23 and 24, dependent on an amended claim, are determined to be patentable.

New claims 25-37 are added and determined to be patentable.

Claim 10 was not reexamined.

1. A video camera head comprising an objective lens assembly and a CMOS sensor; wherein the CMOS sensor comprises an array of photosensitive elements and electronics adapted to deal with the output signals of the photosensitive elements the electronics implemented together with the array of photosensitive elements on a silicon substrate and in that the silicon substrate [comprises] *consists of* no more than two, three, or four electrical connecting pads configured to allow video signals to be sent from the electronics *through at least one wire extending from the video camera head to a video processing unit* and *to allow* power to be supplied to the electronics.

4. [The video camera head of claim 1, wherein] *A video camera head comprising an objective lens assembly and a CMOS sensor; wherein the CMOS sensor comprises an array of photosensitive elements and electronics adapted to deal with the output signals of the photosensitive elements the electronics implemented together with the array of photosensitive elements on a silicon substrate and in that the silicon substrate consists of no more than two, three, or four electrical connecting pads configured to allow video signals to be sent from the electronics and power to be supplied to the electronics, and* the video camera head has a maximum outer diameter of 1.4 mm or less.

5. [The video camera head of claim 1] *A video camera head comprising an objective lens assembly and a CMOS sensor; wherein the CMOS sensor comprises an array of photosensitive elements and electronics adapted to deal with the output signals of the photosensitive elements the electronics implemented together with the array of photosensitive elements on a silicon substrate and in that the silicon substrate consists of no more than two, three, or four electrical connecting pads configured to allow video signals to be sent from the electronics and power to be supplied to the electronics,* wherein the electrical connections between the electrically connecting pads and the [solid state pick up device] *CMOS sensor* are implemented by means of through silicon vias.

6. The video camera head of claim 1, wherein the photosensitive elements of the [solid state pick up device] *CMOS sensor* are implemented using back side illumination technology.

7. [The video camera head of claim 1,] *A video camera head comprising an objective lens assembly and a CMOS sensor; wherein the CMOS sensor comprises an array of photosensitive elements and electronics adapted to deal with the output signals of the photosensitive elements the electronics implemented together with the array of photosensitive elements on a silicon substrate and in that the silicon substrate consists of no more than two, three, or four electrical connecting pads configured to allow video signals to be sent from the electronics and power to be supplied to the electronics, and* the length of the objective lens assembly is 2.5 mm or less.

8. [The video camera head of claim 1,] *A video camera head comprising an objective lens assembly and a CMOS sensor; wherein the CMOS sensor comprises an array of photosensitive elements and electronics adapted to deal with the output signals of the photosensitive elements the electronics implemented together with the array of photosensitive elements on a silicon substrate and in that the silicon substrate consists of no more than two, three, or four electrical connecting pads configured to allow video signals to be sent from the electronics and power to be supplied to the electronics, further* comprising an iris created by metalizing one surface of one lens of the objective lens assembly and etching the iris therein.

9. [The video camera head of claim 6,] *A video camera head comprising an objective lens assembly and a CMOS sensor; wherein the CMOS sensor comprises an array of photosensitive elements and electronics adapted to deal with the output signals of the photosensitive elements the electronics implemented together with the array of photosensitive elements on a silicon substrate and in that the silicon substrate consists of no more than two, three, or four electrical connecting pads configured to allow video signals to be sent from the electronics and power to be supplied to the electronics, wherein the photosensitive elements of the CMOS sensor are implemented using back side illumination technology, and further* comprising pixel cells having dimensions in the range of 2.2×2.2 microns to 0.9×0.9 microns.

11. A visualization probe comprising illumination means, an objective lens assembly and a CMOS sensor; wherein the CMOS sensor comprises an array of photosensitive elements and electronics adapted to deal with the output signals of the photosensitive elements the electronics implemented together with the array of photosensitive elements on a silicon substrate and in that the silicon substrate [comprises] *consists of* no more than two, three, or four electrical connecting pads configured to allow video signals to be sent from the electronics and power to be supplied to the electronics and wherein the visualization probe has a maximum outer diameter of 4 mm or less.

15. The visualization probe of claim 11, wherein the electrical connections between the electrically connecting pads and the [solid state pick up device] *CMOS sensor* and the integrated circuitry are implemented by means of through silicon vias.

16. The visualization probe of claim 11, wherein the photosensitive elements of the [solid state pick up device] *CMOS sensor* are implemented using back side illumination technology.

20. The visualization probe of claim 17, wherein the articulation section is constructed from a plurality of ring-shaped elements attached to an elongated flexible axially located component of the visualization probe[/medical device], wherein the axially located component passes through the centers of the ring-shaped elements.

22. A medical device comprising a visualization probe comprised of illumination means, an objective lens assembly and a CMOS sensor; wherein the CMOS sensor comprises an array of photosensitive elements and electronics adapted to deal with the output signals of the photosensitive elements the electronics implemented together with the array of photosensitive elements on a silicon substrate and in that the silicon substrate [comprises] *consists of* no more than two, three, or four electrical connecting pads configured to allow video signals to be sent from the electronics and power to be supplied to the electronics and wherein the medical device has a maximum outer diameter of 4 mm or less.

25. *The video camera head of claim 1, wherein at least one of said pads configured to allow video signals to be sent is implemented by multiplexing two or more signals on one pad.*

26. *The video camera head of claim 1, further comprising circuitry for transmitting the video signals on a voltage supply line.*

27. *The video camera head of claim 1, further comprising a top coat polymer covering the objective lens assembly.*

28. *The video camera head of claim 1, wherein the wire extends through a visualization probe comprising one or more of:*
   *a) an articulation section;*
   *b) a working channel.*

29. *The video camera head of claim 28, wherein the articulation section is constructed without any hinges and in one piece.*

30. *The video camera head of claim 29, wherein the articulation section is constructed from one plate, and in which each link is cut from the plate precisely by electromagnetic or mechanical apparatus to form a plurality of elements projecting outward from a spine and the projecting elements are then bent to form the individual vertebrae.*

31. *The video camera head of claim 28, wherein the articulation section is constructed from a plurality of ring-shaped elements attached to an elongated flexible axially located component of the visualization probe, wherein the axially located component passes through the centers of the ring-shaped elements.*

32. *The video camera head of claim 5, wherein each pad is connected to a different through silicon via of said through silicon vias.*

33. *The video camera head of claim 5, wherein the electrical connecting pads are configured to allow video signals to be sent from the electronics through at least one wire extending from the video camera head to a video processing unit, and the wire extends through a cable and is directly connected to one of the through silicon vias.*

34. *A video camera head comprising an objective lens assembly and a CMOS sensor; wherein the CMOS sensor comprises an array of photosensitive elements and electronics adapted to deal with the output signals of the photosensitive elements, the electronics implemented together with the array of photosensitive elements on a silicon substrate, and in that the silicon substrate consists of at least two and no more than four electrical connecting pads configured to allow video signals to be sent from the electronics and to allow power to be supplied to the electronics; and wherein the electrical connections between the pads and the electronics adapted to deal with the output signals are implemented with through silicon vias, and the back side of the silicon substrate is patterned to provide electrical conductivity between the bottoms of the vias and the pads.*

35. *A video camera head comprising an objective lens assembly and a CMOS sensor; wherein the CMOS sensor comprises an array of photosensitive elements and electronics adapted to deal with the output signals of the photosensitive elements, the electronics implemented together with the array of photosensitive elements on a silicon substrate, and in that the silicon substrate consists of four electrical connecting pads configured to allow video signals to be sent from the electronics and power to be supplied to the electronics, wherein one of the pads is for voltage input to supply power to the electronics, one of the pads is for a ground connection, one of the pads is for video signal output, and one of the pads is for shutter timing.*

36. *A visualization probe comprising illumination means, an objective lens assembly and a CMOS sensor; wherein the CMOS sensor comprises an array of photosensitive elements and electronics adapted to deal with the output signals of the photosensitive elements, the electronics implemented together with the array of photosensitive elements on a silicon substrate, and in that the silicon substrate consists of four electrical connecting pads configured to allow video signals to be sent from the electronics and power to be supplied to the electronics, wherein one of the pads is for voltage input to supply power to the electronics, one of the pads is for a ground connection, one of the pads is for video signal output, and one of the pads is for shutter timing, and wherein the visualization probe has a maximum outer diameter of 4 mm or less.*

37. *A medical device comprising a visualization probe comprised of illumination means, an objective lens assembly and a CMOS sensor;*
   *wherein the CMOS sensor comprises an array of photosensitive elements and electronics adapted to deal with the output signals of the photosensitive elements, the electronics implemented together with the array of photosensitive elements on a silicon substrate, and in that the silicon substrate consists of four electrical connecting pads configured to allow video signals to be sent from the electronics and power to be supplied to the electronics, wherein one of the pads is for voltage input to supply power to the electronics, one of the pads is for a ground connection, one of the pads is for video signal output, and one of the pads is for shutter timing, and wherein the medical device has a maximum outer diameter of 4 mm or less.*

\* \* \* \* \*